United States Patent
Ji et al.

(10) Patent No.: US 11,080,816 B2
(45) Date of Patent: Aug. 3, 2021

(54) IMAGE MEASURING AND REGISTERING METHOD

(71) Applicants: Ying Ji, Brooklyn, NY (US); Jiansong Ji, Lishui (CN)

(72) Inventors: Ying Ji, Brooklyn, NY (US); Jiansong Ji, Lishui (CN)

(73) Assignee: Ying Ji, Brooklyn, NY (US)

( * ) Notice: Subject to any disclaimer, the term of this patent is extended or adjusted under 35 U.S.C. 154(b) by 172 days.

(21) Appl. No.: 16/259,328

(22) Filed: Jan. 28, 2019

(65) Prior Publication Data

US 2020/0242727 A1  Jul. 30, 2020

(51) Int. Cl.
| | |
|---|---|
| *G06T 3/00* | (2006.01) |
| *G06T 7/30* | (2017.01) |
| *G06F 17/16* | (2006.01) |
| *A61B 34/20* | (2016.01) |
| *G06F 17/12* | (2006.01) |

(52) U.S. Cl.
CPC ............ *G06T 3/0068* (2013.01); *A61B 34/20* (2016.02); *G06F 17/12* (2013.01); *G06F 17/16* (2013.01); *G06T 7/30* (2017.01); *A61B 2034/2051* (2016.02); *A61B 2034/2055* (2016.02)

(58) Field of Classification Search
CPC ............ G06F 17/12; G06F 17/16; G06T 2207/10081; G06T 2207/10088; G06T 2207/30004; G06T 3/0068; G06T 7/30; G06T 7/33; A61B 2034/2051; A61B 2034/2055; A61B 2034/2068; A61B 2090/363; A61B 2090/364; A61B 2090/374; A61B 34/20

USPC ........................................................ 382/726
See application file for complete search history.

(56) References Cited

U.S. PATENT DOCUMENTS

| | | | | |
|---|---|---|---|---|
| 2005/0148859 | A1* | 7/2005 | Miga ........................ | G06T 7/38 600/410 |
| 2008/0154120 | A1* | 6/2008 | von Jako ................. | A61B 5/06 600/411 |
| 2008/0260222 | A1* | 10/2008 | Kumar .................. | G06T 7/0016 382/128 |
| 2014/0369584 | A1* | 12/2014 | Fan ...................... | A61B 5/1079 382/131 |

(Continued)

*Primary Examiner* — Charles N Appiah
*Assistant Examiner* — Nicole M Louis-Fils
(74) *Attorney, Agent, or Firm* — Syncoda LLC; Feng Ma

(57) ABSTRACT

Methods for measuring and registering positions and directions in image space with that in world space includes: providing an assembly with a tracking tool; the assembly including positional and/or directional objects with positions and available directions measured according to the tracking tool's frame with a measuring piece having a measuring surface for measuring without prior calibration with a measuring tracking tool in a tracking system; placing the assembly on a body and perform scanning; placing a relative tracking tool at the body; in registering time, recording the data for both the relative tracking tool and the tracking tool attached to the assembly; placing a tracking tool on an instrument; in post-registering time, recording both data of the tracking tool attached on the instrument and data of the relative tracking tool; computing converted positions and/or available directions of the tracking tool attached on the instrument in the image space.

16 Claims, 12 Drawing Sheets

(56) References Cited

U.S. PATENT DOCUMENTS

2016/0035108 A1\* 2/2016 Yu .................. A61B 5/0077
                                                    382/131
2018/0185113 A1\* 7/2018 Gregerson ............ G06T 15/08

\* cited by examiner

```
┌─────────────────────────────────────────────────────────────┐
│ Providing an assembly and a tracking tool with six-degree freedom of │
│ positions and directions, wherein:                          │
│ the assembly includes: either at least four noncoplanar positional objects, │
│ or at least one positional and at least three orthogonal directional objects; │
│ all objects are rigidly placed in the assembly;             │
│ the tracking tool is removably attached on the assembly rigidly, such │
│ that the position and direction of the objects and of the tracking tool are │
│ fixed relatively each other;                                │
│ the three-dimensional positions and available directions of the objects │
│ are measured regarding to the tracking tool's frame;        │
│ and the objects can be scanned with imaging systems and can be │
│ obtained the three-dimensional positions and available directions for the │
│ objects in the scanned image space;                         │
└─────────────────────────────────────────────────────────────┘
                              │
                              ▼
┌─────────────────────────────────────────────────────────────┐
│ Placing the assembly on a body rigidly and taking imaging scanning │
│ with an imaging system; and through the scanned images, via imaging │
│ processing, obtaining the three-dimensional positions and available │
│ directions for objects in the scanned image space;          │
└─────────────────────────────────────────────────────────────┘
                              │
                              ▼
┌─────────────────────────────────────────────────────────────┐
│ Computing a transformation of converting positions and directions │
│ from world space into image space, based on the measured positions │
│ and available directions of the objects in world space regarding to the │
│ tracking tool's frame and the obtained positions and available │
│ directions of the objects in the image space;               │
└─────────────────────────────────────────────────────────────┘
                              │
                              ▼
┌─────────────────────────────────────────────────────────────┐
│ Placing a relative tracking tool with six-degree freedom on or in the │
│ body; with a tracking system, in the same time referred as registering │
│ time, recording the data of six-degree freedom of directions and │
│ positions for both the relative tracking tool and the tracking tool │
│ attached on the assembly with respect to the frame of the tracking │
│ system;                                                     │
└─────────────────────────────────────────────────────────────┘
                              │
                              ▼
```

FIG. 11A

Placing a tracking tool on an instrument to track the instrument's pose; with the tracking system, in the same time referred as post-registering time, recording both the data of positions and/or available directions of the tracking tool attached on the instrument and the data of six-degree freedom of positions and directions of the relative tracking tool with respect to the frame of the tracking system;

Combining the transformation obtained, two tracking tools' data recorded during registering time, and two tracking tools' data recorded during post-registering time, to compute the converted positions and/or available directions of the tracking tool attached on the instrument in the image space.

FIG. 11B

IMAGE MEASURING AND REGISTERING METHOD

BACKGROUND

When using a surgical navigation system to assist a mini-invasive procedure, a registering is needed to map the physical world space with the imaging space of CT/MR scanning for a part of a patient. By registering, a transformation is obtained to correlate a position in the physical world space with that in the imaging world space. The transformation is used to convert a position in the physical world into that in the imaging world. Then during a surgical procedure assisted by a navigation system, a medical instrument, with its physical world position tracked by a tracking system, can be virtually transformed and displayed in the image world with the scanned patient images.

The registering step often needs extra time and extra burden during a surgical procedure for a surgeon to identify positions/directions in the physical world space and to correlate them in the scanned image space.

SUMMARY

The inventor of the present disclosure has recognized that it is inconvenient and time-consuming drawbacks for a surgeon to perform the registering with existing methods.

The present disclosure relates generally to the field of registering world space with imaging space, and more specifically to methods for convenient registering with convenient measuring preparation.

In an aspect, methods are provided for measuring and registering positions and directions in image space with that in world space. The method includes: providing an assembly with a tracking tool attached; the assembly includes positional objects and/or directional objects; the positions and available directions of the objects are measured regarding to the tracking tool's frame with a measuring piece; the measuring piece having measuring surface measures objects' position and/or direction without prior calibration with a measuring tracking tool in a tracking system; placing the assembly on a body and taking imaging scanning; placing a relative tracking tool on or in the body; in registering time, recording the data of for both the relative tracking tool and the tracking tool attached on the assembly; placing a tracking tool on an instrument; in post-registering time, recording both the data of the tracking tool attached on the instrument and the data of the relative tracking tool; computing the converted positions and/or available directions of the tracking tool attached on the instrument in the image space.

In some embodiments, a method of measuring and registering positions and directions in image space with that in world space includes: (a) providing an assembly and a tracking tool with six-degree freedom of positions and directions, wherein: the assembly includes: either at least four noncoplanar positional objects, or at least one positional object and at least three orthogonal directional objects; all objects are rigidly placed in the assembly; the tracking tool is removably attached on the assembly rigidly, such that the position and direction of the objects and of the tracking tool are fixed relatively each other; the three-dimensional positions and available directions of the objects are measured regarding to the tracking tool's frame; and the objects can be scanned with imaging systems and their three-dimensional positions and available directions can be obtained in the scanned image space; (b) placing the assembly on a body rigidly and taking imaging scanning with an imaging system; and through the scanned images, obtaining the three-dimensional positions and available directions of the objects in the scanned image space; (c) computing a transformation of converting positions and directions from world space into image space, based on the measured positions and available directions of the objects in world space regarding to the tracking tool's frame in step a) and the obtained positions and available directions of the objects in the image space in step b); (d) placing a relative tracking tool with six-degree freedom on or in the body; with a tracking system, in the same time referred as registering time, recording the data of six-degree freedom of directions and positions for both the relative tracking tool and the tracking tool attached on the assembly with respect to the frame of the tracking system; (e) placing a tracking tool on an instrument to track the instrument's pose; with the tracking system, in the same time referred as post-registering time, recording both the data of positions and/or available directions of the tracking tool attached on the instrument and the data of six-degree freedom of positions and directions of the relative tracking tool with respect to the frame of the tracking system; (0 combining the transformation obtained in step c), two tracking tools' data recorded during registering time in step d) and two tracking tools' data recorded during post-registering time in step e), to compute the converted positions and/or available directions of the tracking tool attached on the instrument in the image space.

In some embodiments, the transformation is expressed as T, satisfying a relationship: $OBJECTM1_i^T = T * OBJECTW1_i^T$ (1), wherein $OBJECTM1_i^T$ is the transpose matrix of $OBJECTM1_i$, OBJECTM1 represents (x, y, x, 1) with (x, y, z) representing a position in the image space; $OBJECTW1_{i_T}$ is the transpose matrix of $OBJECTW1_i$, OBJECTW1, represents (x, y, z, 1) with (x, y, z) representing a position in world space in the frame of the tracking tool attached on the assembly removable and rigidly. i represents i th position of the objects with i>=4; the form of the 4×4 transform matrix T is as follows:

$$\begin{pmatrix} & & & x \\ & R & & y \\ & & & z \\ 0 & 0 & 0 & 1 \end{pmatrix},$$

wherein R is a 3×3 rotation matrix and x, y, z is coordinates' translation respectively; T is computed by solving simultaneous equations of at least four relationships of (1) for the at least 4 noncoplanar positions.

In some embodiments, the transformation is expressed as T, satisfying a relationship: $OBJECTM2_i = T * OBJECTW2_i$ (2) wherein $OBJECTM2_i$ is the 4×4 matrix and is as follows:

$$\begin{bmatrix} Ax^M & Ay^M & Az^M & x \\ Bx^M & By^M & Bz^M & y \\ Cx^M & Cy^M & Cz^M & z \\ 0 & 0 & 0 & 1 \end{bmatrix},$$

$(Ax^M, Ay^M, Az^M)$ are x, y, z cosine components of direction A in image space; $(Bx^M\ By^M\ Bz^M)$ are x, y, z cosine components of direction B in image space; $(Cx^M\ Cy^M\ Cz^M)$ are x, y, z cosine components of direction C in image space.

x, y, and z are position components in image space; $OBJECTW2_i$ is the 4×4 matrix and is as follows:

$$\begin{bmatrix} Ax^W & Ay^W & Az^W & x \\ Bx^W & By^W & Bz^W & y \\ Cx^W & Cy^W & Cz^W & z \\ 0 & 0 & 0 & 1 \end{bmatrix}$$

$(Ax^W Ay^W Az^W)$ are x, y, z cosine components of direction A in world space; $Bx^W By^W Bz^W)$ are x, y, z cosine components of direction B in world space; $(Cx^W Cy^W Cz^W)$ are x, y, z cosine components of direction C in world space. x, y and z are position components in world space, wherein the positions and directions in world space are in the frame of the tracking tool attached on the assembly removable and rigidly; i represents i-th position of the objects with i>=1; the form of the 4×4 transform matrix T is as follows:

$$\begin{pmatrix} & & & x \\ & R & & y \\ & & & z \\ 0 & 0 & 0 & 1 \end{pmatrix}$$

R is a 3×3 rotation matrix and x, y, z are component's translations; T is obtained by solving at least one equation (2) for at least one position (x, y, z) and three orthogonal directions of A, B and C; R can also be obtained by solving the below equation: M*R=W (3), wherein M is a 3×3 matrix and is as follows:

$$\begin{pmatrix} Ax^M & Ay^M & Az^M \\ Bx^M & By^M & Bz^M \\ Cx^M & Cy^M & Cz^M \end{pmatrix},$$

W is a 3×3 matrix and is as follows:

$$\begin{pmatrix} Ax^W & Ay^W & Az^W \\ Bx^W & By^W & Bz^W \\ Cx^W & Cy^W & Cz^W \end{pmatrix}.$$

In some embodiments, the, during the registering time, the recorded positions and directions for both the tracking tool attached on the assembly and the relative tracking tool can be expressed as 4×4 matrix B and A, respectively; during the post-registering time, the recorded positions and available directions of the tracking tool attached on the instrument can be expressed as 4×4 matrix D; during the post-registering time, the recorded positions and directions of the relative tracking tool can be expressed as 4×4 matrix E; The positions and available directions in image space converted from that in world space for the tracking tool attached on the instrument can be expressed as a 4×4 matrix F, which satisfies a relationship: $F=T*B^{-1}*A*E^{-1}*D$ (4), where T is the computed transformation of converting positions and directions from world space into image space. The form of the 4×4 transform matrix T is as follo $$\begin{pmatrix} & & & x \\ & R & & y \\ & & & z \\ 0 & 0 & 0 & 1 \end{pmatrix}$$

R is a 3×3 rotation matrix and x, y, z are coordinates' translations; the 4×4 matrix of B, A, E, D and F is as follows:

$$\begin{pmatrix} & & & x \\ & R & & y \\ & & & z \\ 0 & 0 & 0 & 1 \end{pmatrix}$$

R is the 3×3 rotation matrix. x, y, z are the component positions; with the instrument tracking tool's three positional data (x, y, z) in world space with respect to the frame of the tracking system, its corresponding image positions can be computed via equation (4); With the instrument tracking tool's directional data in world space with respect to the frame of the tracking system, its corresponding directions in image space can be computed via equation (4).

In some embodiments, there are more than one assembles and/or there are more than one tracking tools attached on the assembly(s) removably, and/or there are more than one relative tracking tools on or in the body, and/or the relative tracking tool(s) on or in the body is(are) combined with the tracking tool(s) attached on the assembly.

In some embodiments, the tracking tool with six-degree freedom of position and directions is composed with several tracking tools with less than six-degree freedom.

In some embodiments, the third orthogonal direction can be deduced from two orthogonal directions.

In some embodiments, the tracking system is at least one of electromagnetic tracking systems or optical tracking systems.

In some embodiments, the positions of positional objects included in the assembly are measured regarding to the frame of the tracking tool attached on the assembly, the measuring method including: a) letting the object have a convex measuring surface, configured to be part or whole of a sphere, such that the center of the convex measuring surface substantially corresponds to the position of the object to be measured; b) providing a measuring piece having a concave measuring surface substantially fitting with the convex measuring surface of the object; c) attaching a six-degree freedom's tracking tool onto the measuring piece rigidly; d) keeping the measuring piece's concave measuring surface touching seamlessly the convex measuring surface of the object, such that the center of the concave measuring surface unchanged, while moving the measuring piece at different positions; applying a tracking system, recording the data of directions and positions at at least two different positions of the tracking tool attached on the measuring piece with regarding to the frame of the tracking system, in the same time, recording the data of directions and positions of the tracking tool attached on the assembly with regarding to the frame of the tracking system; e) with the recorded data in d), computing the unchanged position of the center of the concave measuring surface of the measuring piece or the unchanged position of the object with regarding to the frame of the tracking tool attached on the assembly.

In some embodiments, the object includes a first portion and a second portion; and the first portion has a shape of a sphere and is substantially at a core center of the spherical object; and the second portion is at an outer layer of the spherical object and is arranged such that a core center of the second portion also substantially coincides with the core center of the first portion; and the first portion and the second portion have different compositions capable of generating a relatively either weak or strong signal compared each other by a diagnostic imaging scanner, as such, in the scanned imaging, the image position of center of the first portion of the object can be determined and measured easily and accurately with distinguishingly displayed spot.

In some embodiments, the recorded data of the tracking tool attached on the measuring piece can be expressed as $4\times4$ matrix $B_i$; the recorded data of the tracking tool attached on the assembly can be expressed as $4\times4$ matrix $A_i$; the pose of the tracking tool attached on the measuring piece in the frame of the tracking tool attached on the assembly can be expressed as $4\times4$ matrix $C_i$, satisfying a relationship: $C_i = A^{-1} * B_i$ (5), the form of the $4\times4$ transform matrices $A_i$, $B_i$ and $C_i$ are as follows:

$$\begin{pmatrix} & & & x \\ & R & & y \\ & & & z \\ 0 & 0 & 0 & 1 \end{pmatrix};$$

R is the $3\times3$ rotation matrix. x, y, z are the component positions. i represents i-th position with i>=2;

the unchanged position of the center of the concave measuring surface of the measuring piece in the frame of the tracking tool attached on the assembly can be expressed by $X_S$, $Y_S$, $Z_S$, satisfying a relationship:

$X_S = X_{B_i} + X_o*C_i(1,1) + Y_o*C_i(2,1) + Z_o*C_i(3,1)$ $Y_S = Y_{B_i} + X_o*C_i(1,2) + Y_o*C_i(2,2) + Z_o*C_i(3,2)$ $Z_S = Z_{B_i} + X_o*C_i(1,3) + Y_o*C_i(2,3) + Z_o*C_i(3,3)$ (6);

$X_O$, $Y_O$, $Z_O$ are the offset distances from the measuring tracking tool's center to the core center of the concave measuring surface. $C_i(m, n)$ are the rotation elements of matrix $C_i$, $X_{B_i}$, $Y_{B_i}$, $Z_{B_i}$ are the X, Y, Z positions of matrix $C_i$. Solving at least two group of equation (6) with i>=2 to obtain the measured position ($X_S$, $Y_S$, $Z_S$) of the core center of the concave measuring surface or the center of the object in the frame of the tracking tool attached on the assembly.

In some embodiments, the recorded data of the tracking tool attached on the measuring piece with regarding to the frame of the tracking system can be expressed as $4\times4$ matrix $B_i$; the recorded data of the tracking tool attached on the assembly with regarding to the frame of the tracking system can be expressed as $4\times4$ matrix $A_i$; the form of the $4\times4$ transform matrices $A_i$ and $B_i$ are as follows:

$$\begin{pmatrix} & & & x \\ & R & & y \\ & & & z \\ 0 & 0 & 0 & 1 \end{pmatrix};$$

R is the $3\times3$ rotation matrix. x, y, z are the component positions. i represents i th position with i>=2; the unchanged position of the center of the concave measuring surface of the measuring piece in the frame of the tracking system can be expressed by $X_S$, $Y_S$, $Z_S$, satisfying a relationship:

$X_S = X_{B_i} + X_O*B_i(1,1) + Y_O*B_i(2,1) + Z_O*B_i(3,1)$ $Y_S = Y_{B_i} + X_O*B_i(1,2) + Y_O*B_i(2,2) + Z_O*B_i(3,2)$ $Z_S = Z_{B_i} + X_O*B_i(1,3) + Y_O*B_i(2,3) + Z_O*B_i(3,3)$ (7);

$X_O$, $Y_O$, $Z_O$ are the offset distances from the measuring tracking tool's center to the core center of the concave measuring surface. $B_i(m, n)$ are the rotation elements of matrix $B_i$, $X_{B_i}$, $Y_{B_i}$, $Z_{B_i}$ are the X, Y, Z position of matrix $B_i$. Solving at least two group of equation (7) with i>=2 to get the measured position ($X_S$, $Y_S$, $Z_S$) of the center of the concave measuring surface or of the object in the frame of the tracking system;

letting AA represent the inverse of mean of group of A or one of A, and (X's, Y's, Z's) represent the measured position of the center of the concave measuring surface or of the object in the frame of the tracking tool attached on the assembly, obtaining (X's, Y's, Z's) based on:

$X'_S = X_B + X_S*AA(1,1) + Y_S*AA(2,1) + Z_S*AA(3,1)$ $Y'_S = Y_B + X_S*AA(1,2) + Y_S*AA(2,2) + Z_S*AA(3,2)$ $Z'_S = Z_B + X_S*AA(1,3) + Y_S*AA(2,3) + Z_S*AA(3,3)$ (8);

AA(m, n) are the rotation elements of matrix AA. $X_B$, $Y_B$, $Z_B$ are the X, Y, Z position of matrix AA.

In some embodiments, the directions of directional objects included in the assembly are measured regarding to the frame of the tracking tool attached on the assembly, the measuring method comprising: a) having the directional object with partial or full cylindrical convex groove's measuring surface or otherwise elongated measuring surface, comprising at least a first partial or full circular cross section, and a second partial or full circular cross section apart, such that the axis of the groove or the elongated object is coincident with the direction of the directional object; b) providing a measuring piece having a concave groove or partial or full-cylindrical cavity measuring surface, comprising at least two concave partial or full circular cross section, substantially fitting with the convex measuring surface of the directional object; c) attaching a tracking tool, which is at least for directional tracking, onto the measuring piece rigidly; d) keeping the measuring piece's concave measuring surface touching seamlessly the convex measuring surface of the object, such that the direction of axis of the concave measuring surface unchanged, while rotating the measuring piece at different rotation angels; applying a tracking system, in the same time, recording both the data of directions at least two different rotation angels of the tracking tool attached on the measuring piece with regarding to the frame of the tracking system, and the data of directions and positions of the tracking tool attached on the assembly with regarding to the frame of the tracking system; e) with the recorded data in d), computing the unchanged direction of the axis of the concave measuring surface of the measuring piece or of the object with regarding to the frame of the tracking tool attached on the assembly.

In some embodiments, the directional object comprises a first portion and a second portion; and the first portion has an elongated shape and is arranged such that its axis coincides with the axis of the directional object; and the second portion is at an outer layer of the object and is arranged such that the axis of the second portion also substantially coincides with the axis of the first portion; and the first portion and the second portion have different compositions capable of generating a relatively either weak or strong signal compared each other by a diagnostic imaging scanner, as such, in the scanned imaging, the image direction of the first portion of the object can be determined and measured easily and accurately with distinguishingly displayed line.

In some embodiments, the recorded data of the tracking tool attached on the measuring piece with regarding to the frame of the tracking system can be expressed as 4×4 matrix $B_i$; the recorded data of the tracking tool attached on the assembly with regarding to the frame of the tracking system can be expressed as 4×4 matrix $A_i$; wherein the form of the 4×4 transform matrices $A_i$, and $B_i$ are as follows:

$$\begin{pmatrix} & & & x \\ & R & & y \\ & & & z \\ 0 & 0 & 0 & 1 \end{pmatrix};$$

wherein R is the 3×3 rotation matrix. x, y, z are the component positions. i represents i th position with i>=2; the unchanged direction of axis of the concave measuring surface of the measuring piece in the frame of the tracking system can be expressed by δx δy, δz, satisfying a relationship:

$$\delta_x = X_{off} * B_i(1,1) + Y_{off} * B_i(2,1) + Z_{off} * B_i(3,1)$$

$$\delta_y = X_{off} * B_i(1,2) + Y_{off} * B_i(2,2) + Z_{off} * B_i(3,2)$$

$$\delta_z = X_{off} * B_i(1,3) + Y_{off} * B_i(2,3) + Z_{off} * B_i(3,3) \quad (9);$$

$X_{off}$, $Y_{off}$, $Z_{off}$ are the component directional offsets/calibration parameters between the direction of the tracking tool attached on the measuring piece and the direction of axis of the concave measuring surface of the measuring piece; $B_i(m, n)$ are the rotation elements of matrix B, Solving at least two group of equation (9) with i>=2 to get the measured direction (δx, δy, δz) of axis of the concave measuring surface of the measuring piece in the frame of the tracking system;

letting AA represent the inverse of mean of group of $A_i$ or one of $A_i$, and (δ'x, δ'y, δ'z) represent the measured direction of axis of the concave measuring surface of the measuring piece or of the directional object in the frame of the tracking tool attached on the assembly, computing (δ'x, δ'y, δ'z) from:

$$\delta'x = \delta x * AA(1,1) + \delta y * AA(2,1) + \delta z * AA(3,1)$$

$$\delta'y = \delta x * AA(1,2) + \delta y * AA(2,2) + \delta z * AA(3,2)$$

$$\delta'z = \delta x * AA(1,3) + \delta y * AA(2,3) + \delta z * AA(3,3) \quad (10),$$

wherein AA(m, n) are the rotation elements of matrix AA.

In some embodiments, the recorded data of the tracking tool attached on the measuring piece can be expressed as 4×4 matrix $B_i$; the recorded data of the tracking tool attached on the assembly can be expressed as 4×4 matrix $A_i$; the pose of the tracking tool attached on the measuring piece in the frame of the tracking tool attached on the assembly can be expressed as 4×4 matrix $C_i$, satisfying a relationship:

$$C_i = A_i^{-1} * B_i \quad (11),$$

the form of the 4×4 transform matrices $A_i$, $B_i$ and $C_i$ are as follows:

$$\begin{pmatrix} & & & x \\ & R & & y \\ & & & z \\ 0 & 0 & 0 & 1 \end{pmatrix};$$

wherein R is the 3×3 rotation matrix. x, y, z are the component positions. i represents i-th position with i>=2; the unchanged direction of axis of the concave measuring surface of the measuring piece or of the object in the frame of the tracking tool attached on the assembly can be expressed by (δ'x, δ'y, δ'z), satisfying a relationship:

$$\delta'x = X_{off} * C_i(1,1) + Y_{off} * C_i(2,1) + Z^{off} * C_i(3,1)$$

$$\delta'y = X_{off} * C_i(1,2) + Y_{off} * C_i(2,2) + Z_{off} * C_i(3,2)$$

$$\delta'z = X_{off} * C_i(1,3) + Y_{off} * C_i(2,3) + Z_{off} * C_i(3,3) \quad (12)$$

$X_{off}$, $Y_{off}$, $Z_{off}$ are the component directional offsets/calibration parameters between the direction of the tracking tool attached on the measuring piece and the direction of axis of the concave measuring surface of the measuring piece; $C_i(m, n)$ are the rotation elements of matrix $C_i$ Solving at least two group of equation (12) with i>=2 to get the measured direction of axis of the concave measuring surface of the measuring piece or of the directional object in the frame of the tracking tool attached on the assembly.

BRIEF DESCRIPTION OF THE DRAWINGS

FIG. 11A is a first part of a flow chart of registering positions and directions in image space with that in world space; and FIG. 11B is a second part of the flow chart of registering positions and directions in image space with that in world space.

DETAILED DESCRIPTION

Figure 1:
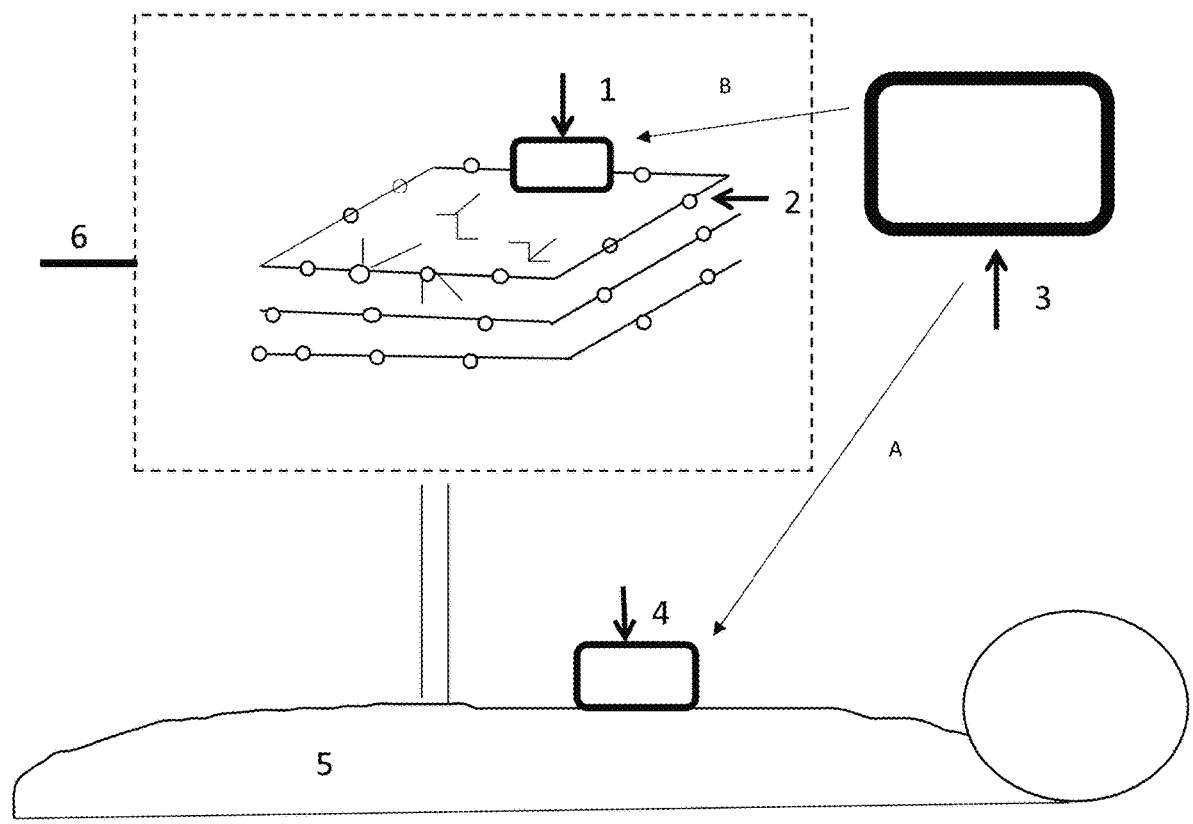
FIG. 1 is a schematic diagram of registering with a tracking system.

FIG. 1 illustrates a diagram overview of registering with a tracking system. As shown in the figure, a tracking tool 4 is attached on the patient body 5 (at the surface of the patient body or inside the patient body) and is considered as a relative reference tracking tool. A register assembly 6 includes a tacking tool 1 attached and a special part, which is composed of either at least four noncoplanar positional objects 2, or at least one positional and at least three orthogonal directional objects 2. The said special part can be in some shape, such as dot, sphere, line, curve, etc., as long as there are either at least four noncoplanar positional objects 2, or at least one positional and at least three orthogonal directional objects 2 included. Each of objects 2 mathematically and ideally has unique three-dimensional position and/or unique direction in physical world.

The tracking tool 1 is considered as a register tracking tool. The register assembly 6 is rigid such that each position and direction of the tracking tool 1 and of the objects 2 are fixed relatively each other. The positions and available directions of objects 2 can be measured regarding to the register tracking tool 1's frame via various methods and the measurement is considered as preparation for the register assembly 6 to be used.

The said special part composed of either at least four noncoplanar positional objects 2, or least one positional and at least three orthogonal directional objects 2, can be scanned with CT/MR systems or other machines. The objects 2 can be displayed in the scanned images with known three-dimensional positions and available directions.

As shown in FIG. 1, the reference tracking tool 4 and the register tracking tool 1 are coupled to a tracking apparatus, wirelessly or by wires, and obtain respectively six-degree both position and direction parameters regarding to the tracking apparatus's frame (for example, the transmitter 3's frame) via the tracking apparatus/system.

In the following sections, measuring for preparing the assembly 6 and registering with tracking tool 1 and tool 4 are described.

Section 1 Measuring for Preparing the Assembly

There are two parameters needing to measure for objects 2 in the frame of the tracking tool attached on the assembly. One is the position. Another is the direction.

Section 1.1 Position Measurement

Some known method for measuring the positions of the objects 2 is to apply an electromagnetic tracking system. Place the register assembly 6 in the trackable region; use a register pen, with known tip position with respect to the tracking system, to touch its tip with each of objects 2; obtain each of objects 2's position regarding to the frame of the tracking system; in the same time, record the register tracking tool 1's pose data regarding to the frame of the tracking system; then compute and convert the each of objects 2's position regarding to the frame of the tracking system into the position regarding to the frame of the register tracking tool 1.

The present disclosure describes a method to measure the position without necessarily measuring the tip position of the pen.

The electromagnetic tracking system generally comprises tracking tools and a transmitter 3. The transmitter 3 is configured to generate electromagnetic fields. The tracking tool usually comprises a sensing coil, configured to produce an induced voltage in the electromagnetic field. The tracking system further comprises an electronics unit, coupled to the sensing coil and the transmitter, and configured to calculate the position and direction data of the tracking tool based on the induced voltage produced in the sensing coil.

Figure 2:
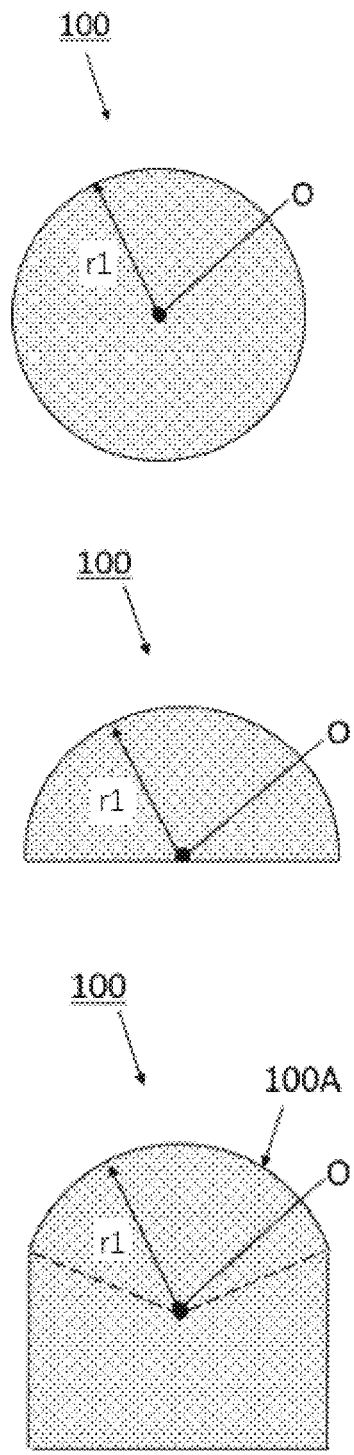
FIG. 2 illustrates a spherical object with convex measuring surface.
Figure 3:
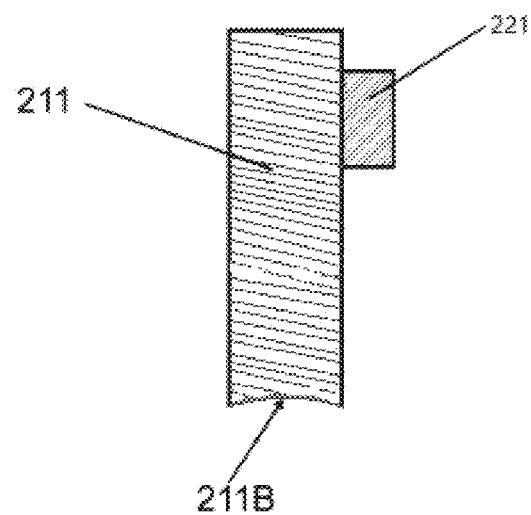
FIG. 3 illustrates a measuring piece with a tracking tool attached for positional measuring.
Figure 3:
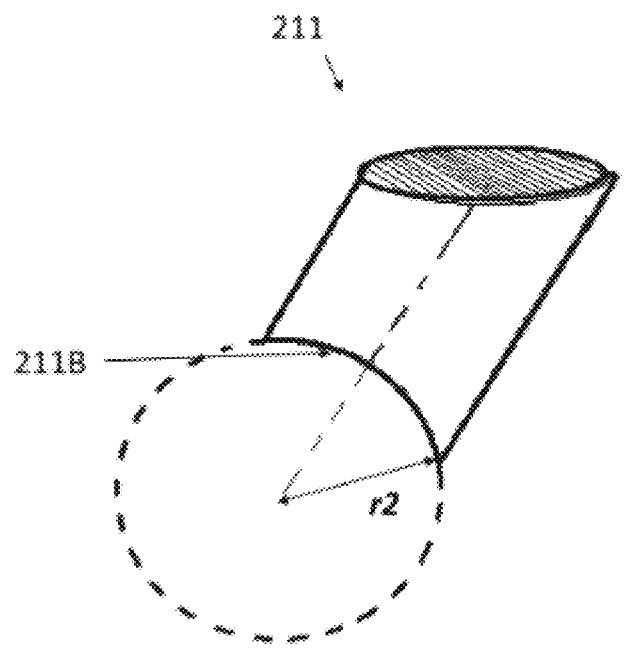
Figure 4:
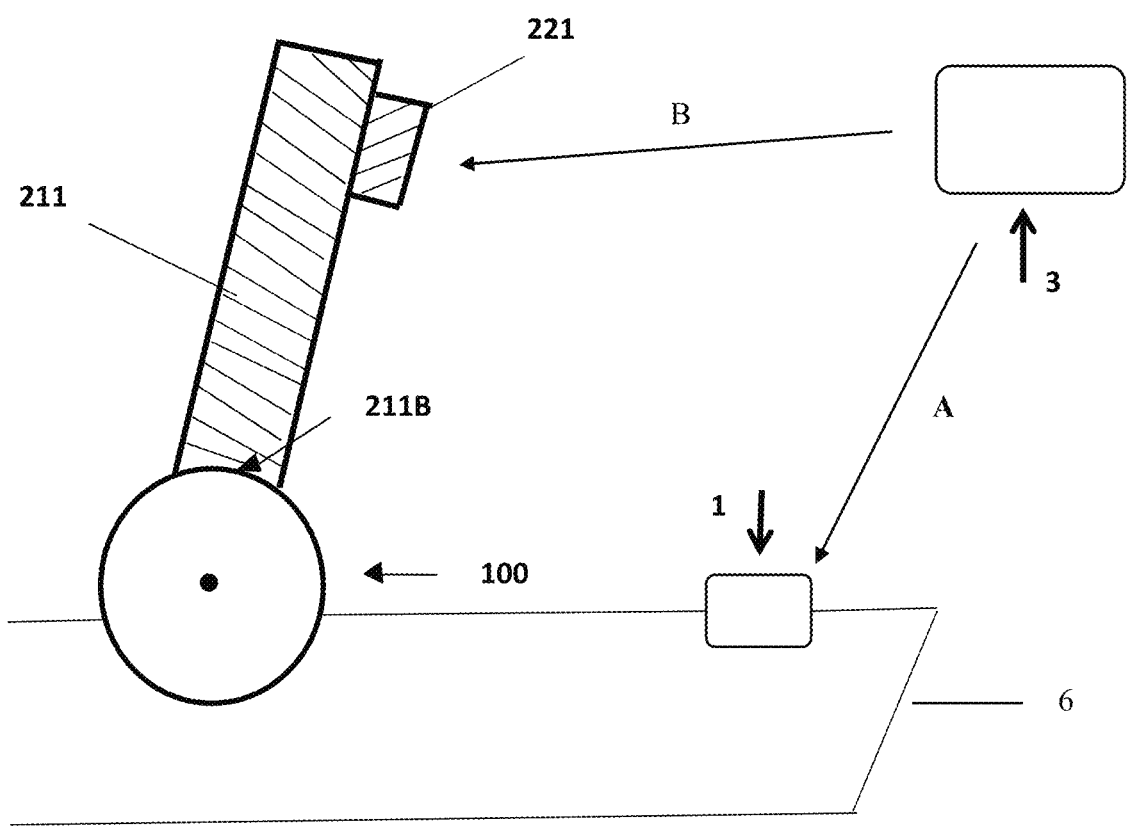
FIG. 4 is a is a schematic diagram of measuring positions with a tracking system.

An embodiment to measure the positions of the objects 2 regarding to the frame of the tracking tool 1 attached on the assembly comprises:

a) letting the object have a convex measuring surface, configured to be part or whole of a sphere, such that the center of the convex measuring surface substantially corresponds to the position of the object to be measured;

As shown in FIG. 2, the object 100 has a convex measuring surface 100A, the radius of the spherical object is r1, the center of convex measuring surface is O.

b) providing a measuring piece having a concave measuring surface substantially fitting with the convex measuring surface of the object;

c) attaching a six-degree freedom's tracking tool onto the measuring piece rigidly;

As shown in FIG. 3, the measuring piece 211 has a concave measuring surface 211B. A tracking tool 221 is attached on the measuring piece 211. The concave measuring surface 211B has radius r2, which is substantially the same as the radius r1 of the sphere of the convex surface in object 100.

d) keeping the measuring piece's concave measuring surface touching seamlessly the convex measuring surface of the object, such that the center of the concave measuring surface unchanged, while moving the measuring piece at different positions; applying a tracking system, recording the data of directions and positions at least two different positions of the tracking tool attached on the measuring piece with regarding to the frame of the tracking system, in the same time, recording the data of directions and positions of the tracking tool attached on the assembly with regarding to the frame of the tracking system;

As shown in FIG. 4, both the data for tracking tool 221 attached on the measuring piece 211 and the data for tracking tool 1 attached on the assembly are recorded in the same time, while keeping the measuring piece's concave measuring surface 211B touching seamlessly the convex measuring surface of the object 100 and moving the measuring piece 211 at different positions. The transmitter 3 is configured to generate an electromagnetic field.

e) with the recorded data in d), computing the unchanged position of the center of the concave measuring surface of the measuring piece or the unchanged position of the object with regarding to the frame of the tracking tool attached on the assembly.

In some embodiments, the object comprises a first portion and a second portion; and the first portion has a shape of a sphere and is substantially at a core center of the spherical object; and the second portion is at an outer layer of the spherical object and is arranged such that a core center of the second portion also substantially coincides with the core center of the first portion; and the first portion and the second portion have different compositions capable of generating a relatively either weak or strong signal compared each other by a diagnostic imaging scanner, as such, in the scanned imaging, the image position of center of the first portion of the object can be determined and measured easily and accurately with distinguishingly displayed spot.

Figure 5A:
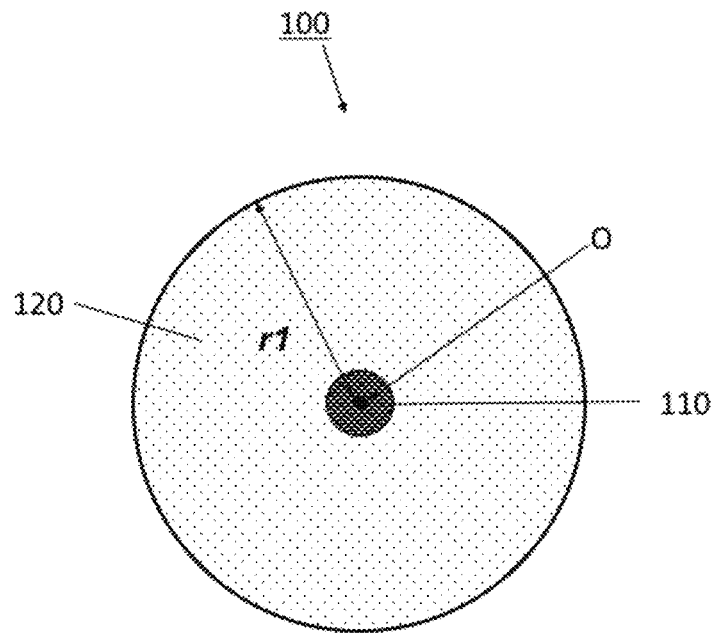
FIG. 5A is a cross-sectional view of the two-portion object having a spherical shape.

FIG. 5A is a cross-sectional view of the two-portion object. As illustrated, the object 100 is substantially a spherical object having a radius of r1. The first portion 110 has a shape of a small sphere and is substantially at a core center of the spherical object 100 (i.e., a core center of the first portion 110 substantially coincides with the core center of the spherical object 100). The second portion 120 is at an outer layer of the spherical object 100, and is arranged such that a core center of the second portion 120 also substantially coincides with the core center of the first portion 110.

Figure 5B:
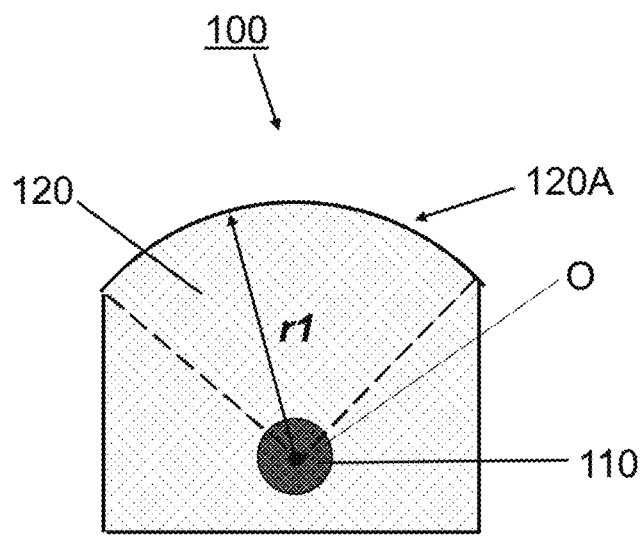
FIG. 5B is a cross-sectional view of the two-portion object having a non-spherical shape.

FIG. 5B shows a cross-sectional view of an object 100 having a non-spherical shape according to some other embodiment. Similar to the embodiment of the object as illustrated in FIG. 5A, the object 100 also comprises a first portion 110 having a shape of a small sphere and is embedded in the second portion 120. The second portion 120 comprises a convex surface 120A (as indicated by the arrow in FIG. 5B), configured to be a portion of a sphere having a radius of r1. It is configured such that the first portion 110 is substantially at a core center of the convex surface 120A of the second portion 120 (i.e., the core center of the convex surface 120A of the second portion 120 is substantially a core center of a sphere to which the convex surface 120A belongs).

In addition to the arrangement of the first portion 110 and the second portion 120 in the object 100 as illustrated in FIGS. 5A and 5B, other arrangements are also possible. For example, the first portion 110 can be on a surface of the second portion 120, as long as the first portion, still as a small sphere, is substantially at a core center of a convex surface 120A of the second portion 120.

In some embodiments, the recorded data of the tracking tool attached on the measuring piece can be expressed as 4×4 matrix $B_i$; the recorded data of the tracking tool attached on the assembly can be expressed as 4×4 matrix $A_i$, as shown in FIG. 4. The pose of the tracking tool attached on the measuring piece in the frame of the tracking tool attached on the assembly can be expressed as 4×4 matrix $C_i$, satisfying a relationship:

$$C_i = A_i^{-1} * B_i \qquad (1).$$

The form of the 4×4 transform matrices $A_i$, $B_i$ and $C_i$ are as follows:

$$\begin{pmatrix} & & & x \\ & R & & y \\ & & & z \\ 0 & 0 & 0 & 1 \end{pmatrix}.$$

R is the 3×3 rotation matrix. x, y, z are the component positions. i represents i th position with i>=2.

the unchanged position of the center of the concave measuring surface of the measuring piece in the frame of the tracking tool attached on the assembly can be expressed by $X_S$, $Y_S$, $Z_S$, satisfying a relationship:

$$X_S = X_{B_i} + X_O * C_i(1,1) + Y_O * C_i(2,1) + Z_O * C_i(3,1)$$

$$Y_S = Y_{B_i} + X_O * C_i(1,2) + Y_O * C_i(2,2) + Z_O * C_i(3,2)$$

$$Z_S = Z_{B_i} + X_O * C_i(1,3) + Y_O * C_i(2,3) + Z_O * C_i(3,3) \qquad (2)$$

$X_O$, $Y_O$, $Z_O$ are the offset distances from the measuring tracking tool's center to the core center of the concave measuring surface. $C_i(m, n)$ are the rotation elements of matrix $C_i$. $X_{B_i}$, $Y_{B_i}$, $Z_{B_i}$ are the X, Y, Z positions of matrix $C_i$. Solving at least two group of equation (2) with i>=2 gets the measured position ($X_S$, $Y_S$, $Z_S$) of the core center of the concave measuring surface or the center of the object in the frame of the tracking tool attached on the assembly.

In some embodiments, the recorded data of the tracking tool attached on the measuring piece with regarding to the frame of the tracking system can be expressed as 4×4 matrix $B_i$; the recorded data of the tracking tool attached on the assembly with regarding to the frame of the tracking system can be expressed as 4×4 matrix A as shown in FIG. 4.

The form of the 4×4 transform matrices $A_i$, and $B_i$ are as follows:

$$\begin{pmatrix} & & & x \\ & R & & y \\ & & & z \\ 0 & 0 & 0 & 1 \end{pmatrix}$$

R is the 3×3 rotation matrix. x, y, z are the component positions. i represents i th position with i>=2.

the unchanged position of the center of the concave measuring surface of the measuring piece in the frame of the tracking system can be expressed by $X_S$, $Y_S$, $Z_S$, satisfying a relationship:

$$X_S = X_{B_i} + X_O * B_i(1,1) + Y_O * B_i(2,1) + Z_O * B_i(3,1)$$

$$Y_S = Y_{B_i} + X_O * B_i(1,2) + Y_O * B_i(2,2) + Z_O * B_i(3,2)$$

$$Z_S = Z_{B_i} + X_O * B_i(1,3) + Y_O * B_i(2,3) + Z_O * B_i(3,3) \qquad (3).$$

$X_O$, $Y_O$, $Z_O$ are the offset distances from the measuring tracking tool's center to the core center of the concave measuring surface. $B_i(m, n)$ are the rotation elements of matrix $B_i$. $X_{B_i}$, $Y_{B_i}$, $Z_{B_i}$ are the X, Y, Z positions of matrix $B_i$. Solving at least two group of equation (3) with i>=2 gets the measured position ($X_S$, $Y_S$, $Z_S$) of the center of the concave measuring surface or of the object in the frame of the tracking system.

Assume MA to be the mean of group of Ai or one of Ai. Let AA represent the inverse of MA. Let ($X'_S$, $Y'_S$, $Z'_S$) represent the measured position of the center of the concave measuring surface or of the object in the frame of the tracking tool attached on the assembly, ($X'_S$, $Y'_S$, $Z'_S$) can be computed from:

$$X'_S = X_S + X_S * AA(1,1) + Y_S * AA(2,1) + Z_S * AA(3,1)$$

$$Y'_S = Y_S + X_S * AA(1,2) + Y_S * AA(2,2) + Z_S * AA(3,2)$$

$$Z'_S = Z_S + X_S * AA(1,3) + Y_S * AA(2,3) + Z_S * AA(3,3) \qquad (4).$$

AA(m, n) are the rotation elements of matrix AA. $X_S$, $Y_S$, $Z_S$ are the X, Y, Z position of matrix AA.

Section 1.2 Direction Measurement

Figure 6:
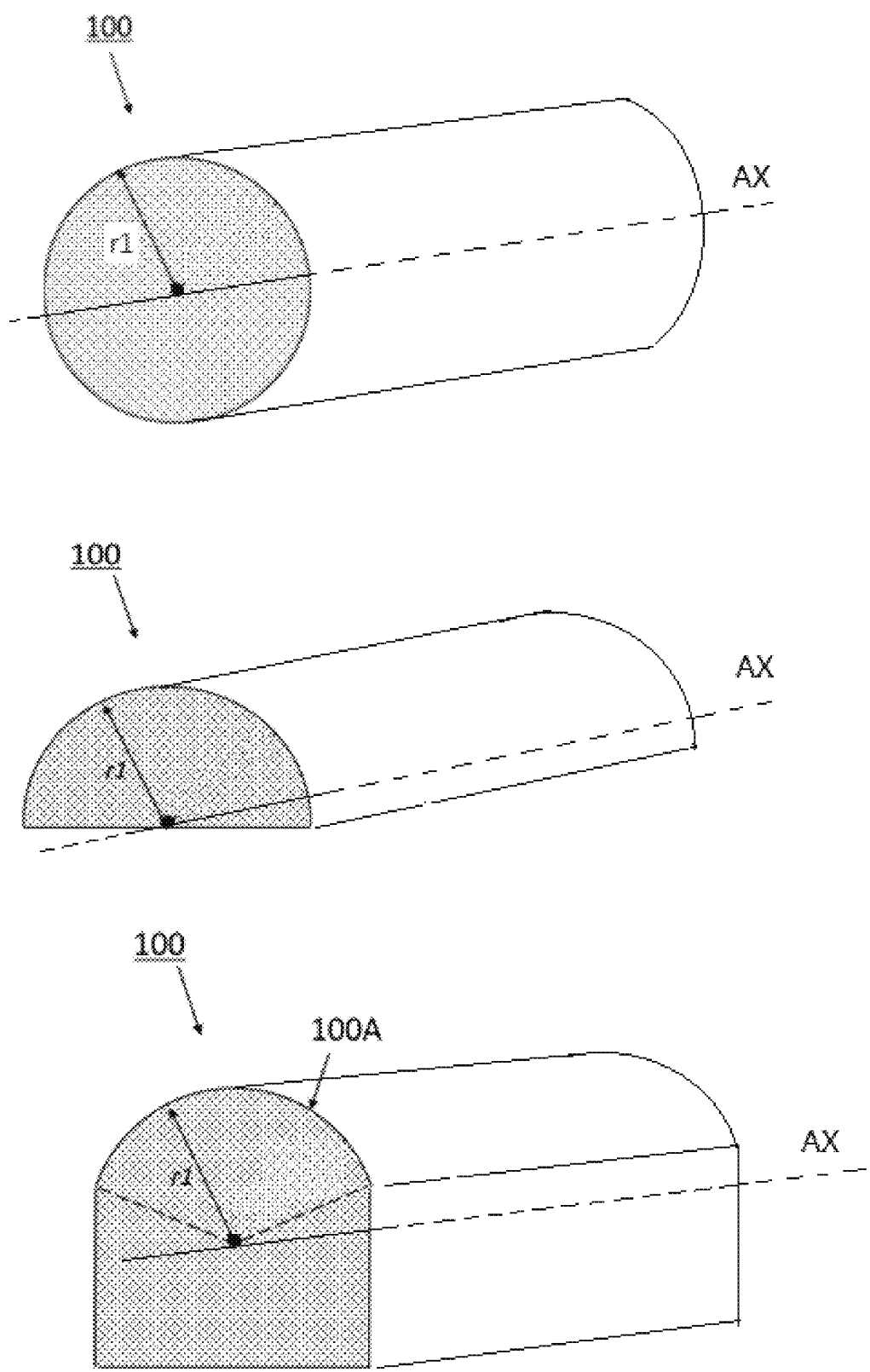
FIG. 6 illustrates an elongated object according to some embodiments of the present disclosure.

An embodiment to measure the directions of directional objects 2 regarding to the frame of the tracking tool 1 attached on the assembly comprises:

a) having the directional object with partial or full cylindrical measuring surface or elongated measuring surface, composed with at least a first partial or full circular cross section, and a second partial or full circular cross section apart, such that the axis of the groove or the elongated object is coincident with the direction of the directional object;

As shown in FIG. 6, the object 100 has a convex measuring surface 100A, the radius of the cylindrical object is r1, the axis of the convex measuring surface of the groove or rod is AX.

Figure 7:
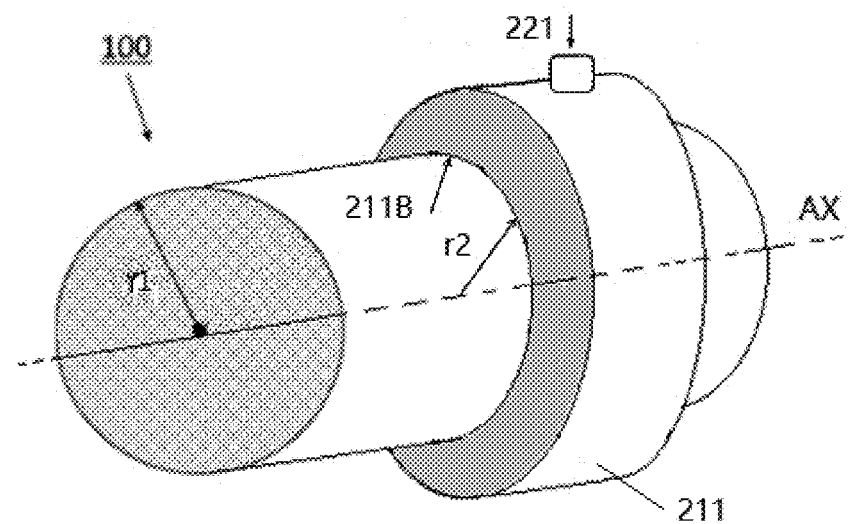
FIG. 7 illustrates a measuring piece having a concave measuring surface with a tracking tool attached for directional positional measuring.
Figure 7:
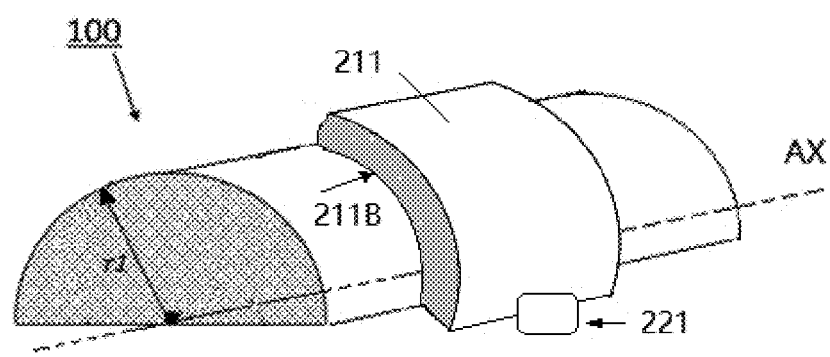
Figure 7:
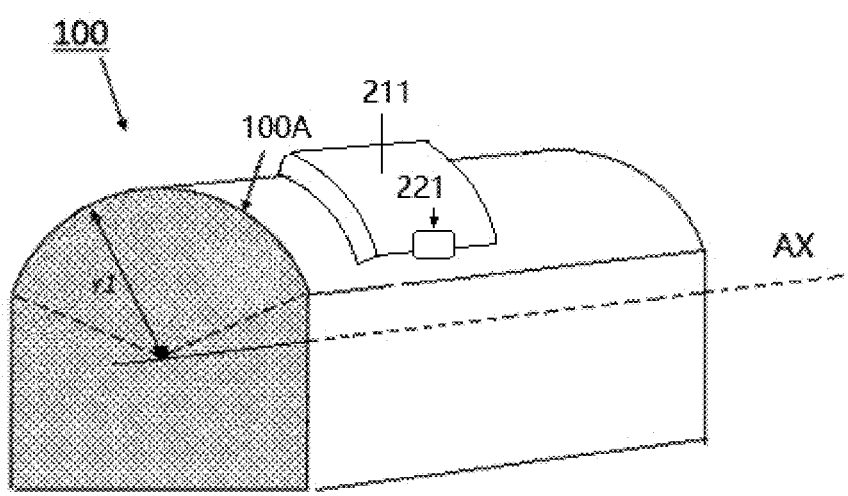
Figure 8:
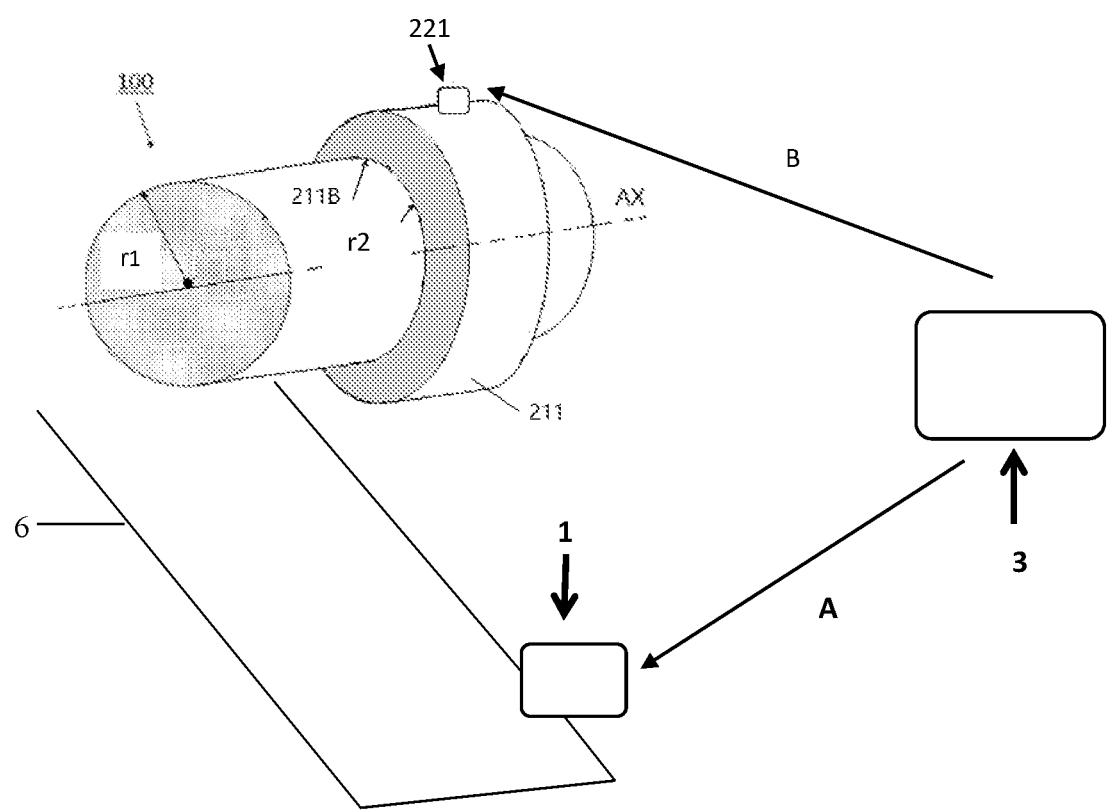
FIG. 8 is a is a schematic diagram of measuring directions with a tracking system.

In some embodiments, the first and the second cross sections have different radii, while the axis of the groove or the elongated object is still coincident with the direction of the directional object;

b) providing a measuring piece having a concave groove or partial or full-cylindrical cavity measuring surface, composed with at least two concave partial or full circular cross section, substantially fitting with the convex measuring surface of the directional object;

c) attaching a tracking tool, which is at least for directional tracking, onto the measuring piece rigidly;

As shown in FIG. 7, the measuring piece 211 has a concave measuring surface 211B. A tracking tool 221 is attached on the measuring piece 211. The concave measuring surface 211B has radius r2, which is substantially the same as the radius r1 of the cylindrical convex surface in object 100.

d) keeping the measuring piece's concave measuring surface touching seamlessly the convex measuring surface of the object, such that the direction of axis of the concave measuring surface unchanged, while rotating the measuring piece at different rotation angels; applying a tracking system, in the same time, recording both the data of directions at at least two different rotation angels of the tracking tool attached on the measuring piece with regarding to the frame of the tracking system, and the data of directions and positions of the tracking tool attached on the assembly with regarding to the frame of the tracking system;

As shown in FIG. 8, the directional data for tracking tool 221 attached on the measuring piece 211 and the directional and positional data for tracking tool 1 attached on the assembly 6 are recorded in the same time, while keeping the measuring piece's concave measuring surface 211B touching seamlessly the convex measuring surface of the object 100 and rotating the measuring piece 211 at different rotating angles. The transmitter 3 is configured to generate an electromagnetic field.

e) with the recorded data in d), computing the unchanged direction of the axis of the concave measuring surface of the measuring piece or the object with regarding to the frame of the tracking tool attached on the assembly In some embodiments, the directional object comprises a first portion and a second portion; and the first portion has an elongated shape and is arranged such that its axis coincides with the axis of the directional object; and the second portion is at an outer layer of the object and is arranged such that the axis of the second portion also substantially coincides with the axis of the first portion; and the first portion and the second portion have different compositions capable of generating a relatively either weak or strong signal compared each other by a diagnostic imaging scanner, as such, in the scanned imaging, the image direction of the first portion of the object can be determined and measured easily and accurately with distinguishingly displayed line.

Figure 9A:
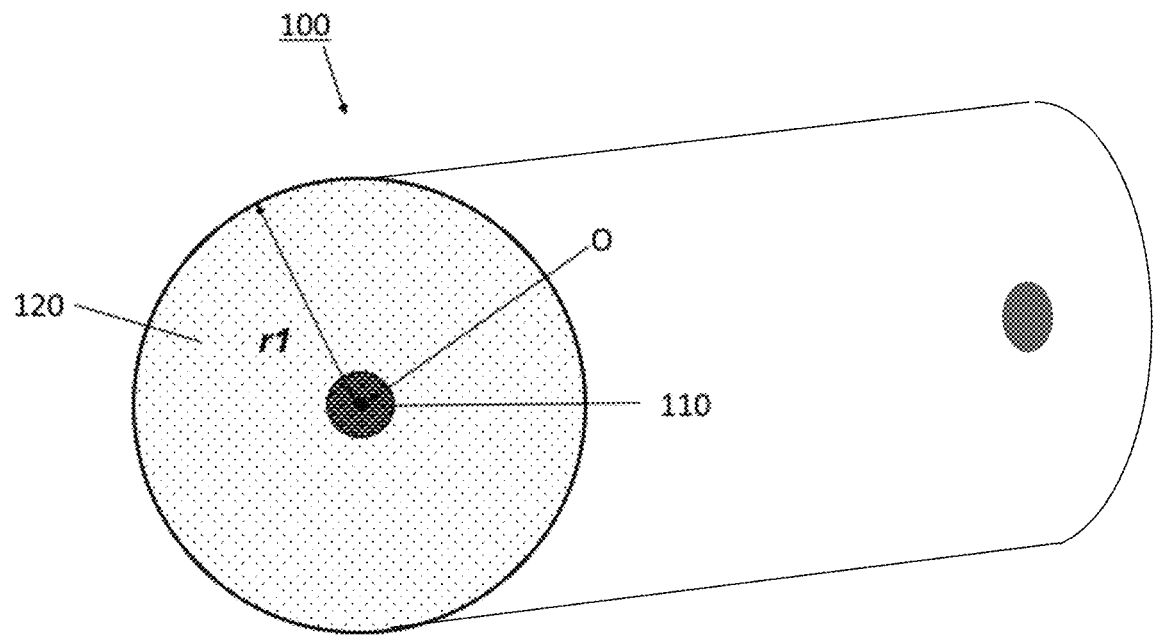
FIG. 9A shows a two-portion object having a cylindrical surface.
Figure 9B:
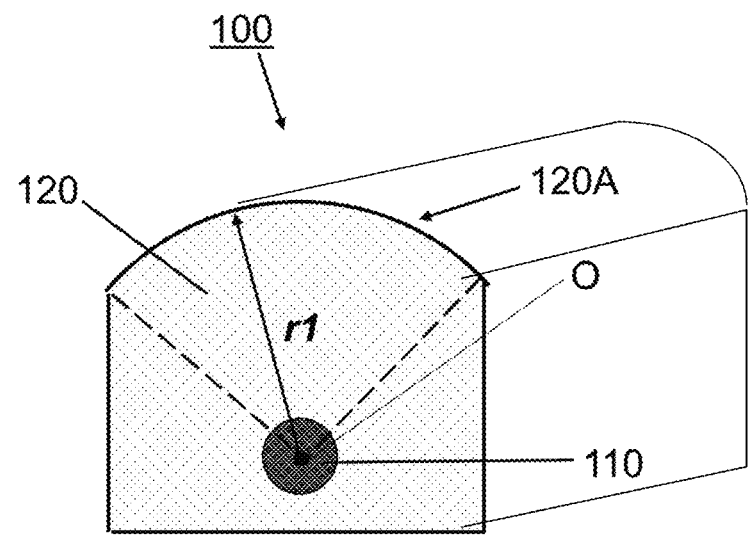
FIG. 9B shows a two-portion object having a partial-cylindrical shape.

FIG. 9 illustrates the two-portion object. As illustrated, the object 100 has portion 110 and portion 120. The first portion 110 has an elongated shape and is arranged such that its axis coincides with the axis of the directional object. The second portion 120 is at an outer layer of the elongated object 100, and is arranged such that the axis of the second portion 120 also substantially coincides with the axis of the first portion 110.

In some embodiments, the recorded data of the tracking tool attached on the measuring piece with regarding to the frame of the tracking system can be expressed as 4×4 matrix $B_i$; the recorded data of the tracking tool attached on the assembly with regarding to the frame of the tracking system can be expressed as 4×4 matrix $A_i$ as shown in FIG. 8.

The form of the 4×4 transform matrices $A_i$ and $B_i$ are as follows:

$$\begin{pmatrix} & & & x \\ & R & & y \\ & & & z \\ 0 & 0 & 0 & 1 \end{pmatrix}$$

R is the 3×3 rotation matrix. x, y, z are the component positions. i represents i th position with i>=2.

the unchanged direction of axis of the concave measuring surface of the measuring piece in the frame of the tracking system can be expressed by δx δy, δz, satisfying a relationship:

$$\delta x = X_{off} * B_i(1,1) + Y_{off} * B_i(2,1) + Z_{off} * B_i(3,1)$$

$$\delta y = X_{off} * B_i(1,2) + Y_{off} * B_i(2,2) + Z_{off} * B_i(3,2)$$

$$\delta z = X_{off} * B_i(1,3) + Y_{off} * B_i(2,3) + Z_{off} * B_i(3,3) \quad (5).$$

$X_{off}$, $Y_{off}$, $Z_{off}$ are the component directional offsets/calibration parameters between the direction of the tracking tool attached on the measuring piece and the direction of axis of the concave measuring surface of the measuring piece. $B_i$(m, n) are the rotation elements of matrix $B_i$ Solving at least two group of equation (5) with i>=2 gets the measured direction (δx, δy, δz) of axis of the concave measuring surface of the measuring piece in the frame of the tracking system.

Assume MA to be the mean of group of Ai or one of Ai. Let AA represent the inverse of MA. Let (δ'x, δ'y, δ'z) represent the measured direction of axis of the concave measuring surface of the measuring piece or the directional object in the frame of the tracking tool attached on the assembly. (δ'x, δ'y, δ'z) can be computed from:

$$\delta' x = \delta x * AA(1,1) + \delta y * AA(2,1) + \delta z * AA(3,1)$$

$$\delta' y = \delta x * AA(1,2) + \delta y * AA(2,2) + \delta z * AA(3,2)$$

$$\delta' z = \delta x * AA(1,3) + \delta y * AA(2,3) + \delta z * AA(3,3) \quad (6),$$

wherein AA(m, n) are the rotation elements of matrix AA.

In some embodiments, the recorded data of the tracking tool attached on the measuring piece can be expressed as 4×4 matrix $B_i$; the recorded data of the tracking tool attached on the assembly can be expressed as 4×4 matrix $A_i$ as shown in FIG. 8. The pose of the tracking tool attached on the measuring piece in the frame of the tracking tool attached on the assembly can be expressed as 4×4 matrix $C_i$, satisfying a relationship:

$$C_i = A_i^{-1} * B_i \quad (7),$$

The form of the 4×4 transform matrices $A_i$, $B_i$ and $C_i$ are as follows:

$$\begin{pmatrix} & & & x \\ & R & & y \\ & & & z \\ 0 & 0 & 0 & 1 \end{pmatrix}.$$

R is the 3×3 rotation matrix. x, y, z are the component positions. i represents i th position with i>=2.

The unchanged direction of axis of the concave measuring surface of the measuring piece or the object in the frame of the tracking tool attached on the assembly can be expressed by (δ'x, δ'y, δ'z), satisfying a relationship:

$$\delta'x = X_{off}*C_i(1,1) + Y_{off}*C_i(2,1) + Z_{off}*C_i(3,1)$$

$$\delta'y = X_{off}*C_i(1,2) + Y_{off}*C_i(2,2) + Z_{off}*C_i(3,2)$$

$$\delta'z = X_{off}*C_i(1,3) + Y_{off}*C_i(2,3) + Z_{off}*C_i(3,3) \qquad (8).$$

$X_{off}$, $Y_{off}$, $Z_{off}$ are the component directional offsets/calibration parameters between the direction of the tracking tool attached on the measuring piece and the direction of axis of the concave measuring surface of the measuring piece.

$C_i(m, n)$ are the rotation elements of matrix $C_i$. Solving at least two group of equation (8) with i>=2 gets the measured direction of axis of the concave measuring surface of the measuring piece or the directional object in the frame of the tracking tool attached on the assembly Section 2 Registering with Tracking Tools Before the surgical procedure, the register assembly 6 is prepared without a patient or a surgeon involved, such that the fixed three-dimensional physical world positions and available directions of objects 2 are known by measuring regarding to the register tracking tool 1's frame. The register tracking tool 1 is removable.

When starting a surgical procedure, rigidly attach the register assembly 6 on the patient, such that the relative position and direction between the register assembly 6 and the patient (more specifically, the region of interested on the patient body) are fixed. Then take the register assembly 6 and the patient together into a scanning machine, obtain the images including the patient and objects 2, and obtain the positions and available directions of objects 2 via some imaging processing.

In some embodiments, objects 2 includes at least four noncoplanar positions. A position of objects 2 in world space can be expressed as $OBJECTW_i\%$ (x, y, z), and its position in image space can be expressed as $OBJECTM_i$ (x, y, z) with i>=4.

With known OBJECTM and OBJECTW, a transform T can be computed via the following equation:

$$OBJECTM1_i^T = T*OBJECTW1_i^T \qquad (9),$$

wherein T is a 4×4 matrix, $OBJECTM1_i^T$ is the transpose matrix for (x, y, z, 1) or $(OBJECTM_i, 1)$ and $OBJECTW1_i^T$ is the transpose matrix for (x, y, z, 1) or $(OBJECTW_i, 1)$. i represents i th position with i>=4.

There are at least four equation (9)s with i>=4. By solving simultaneous equations (9)s, T can be obtained. At this step there is no need for position and direction parameters of the register tracking tool 1 and of the relative reference tracking tool 4.

In some embodiments, objects 2 includes at least one position (x, y, z) and at least three orthogonal direction A, B and C. The transformation is expressed as T, satisfying a relationship:

$$OBJECTM2_i = T*OBJECTW2_i \qquad (10),$$

wherein
$OBJECTM2_i$ is the 4×4 matrix and is as follows:

$$\begin{bmatrix} Ax^M & Ay^M & Az^M & x^M \\ Bx^M & By^M & Bz^M & y^M \\ Cx^M & Cy^M & Cz^M & z^M \\ 0 & 0 & 0 & 1 \end{bmatrix}$$

$(Ax^M, Ay^N, Az^M)$ are x, y, z cosine components of direction A in image space; $(Bx^M By^M Bz^M)$ are x, y, z cosine components of direction B in image space; $(Cx^M Cy^M Cz^M)$ are x, y, z cosine components of direction C in image space. $x^M$, $y^M$ and $z^M$ are position components in image space.

$OBJECTW2_i$ is the 4×4 matrix and is as follows:

$$\begin{bmatrix} Ax^W & Ay^W & Az^W & x^W \\ Bx^W & By^W & Bz^W & y^W \\ Cx^W & Cy^W & Cz^W & z^W \\ 0 & 0 & 0 & 1 \end{bmatrix}$$

$(Ax^W Ay^W Az^W)$ are x, y, z cosine components of direction A in world space; $Bx^W By^W Bz^W)$ are x, y, z cosine components of direction B in world space; $(Cx^W Cy^W Cz^W)$ are x, y, z cosine components of direction C in world space. $x^W$, $y^W$ and $z^W$ are position components in world space. The herein positions and directions in world space are in the frame of the tracking tool attached on the assembly. i represents i th position/direction of objects 2 with i>=1.

The form of the 4×4 transform matrix T is as follows:

$$\begin{pmatrix} & & & x \\ & R & & y \\ & & & z \\ 0 & 0 & 0 & 1 \end{pmatrix}$$

R is a 3×3 rotation matrix and x, y, z are component's translations.

T is obtained by solving at least one equation (10) for at least one position (x, y, z) and at least three orthogonal directions of A, B and C.

R can also be obtained by solving the below equation:

$$M*R = W \qquad (11),$$

wherein M is a 3×3 matrix and is as follows:

$$\begin{pmatrix} Ax^M & Ay^M & Az^M \\ Bx^M & By^M & Bz^M \\ Cx^M & Cy^M & Cz^M \end{pmatrix},$$

W is a 3×3 matrix and is as follows:

$$\begin{pmatrix} Ax^W & Ay^W & Az^W \\ Bx^W & By^W & Bz^W \\ Cx^W & Cy^W & Cz^W \end{pmatrix}.$$

At this step there is no need for position and direction parameters of the register tracking tool 1 and of the relative reference tracking tool 4.

The following step is related to the timing and the positioning, and is considered as registering time, wherein the relative reference tracking tool 4 is actively placed on or inside the patient body, and the register tracking tool 1 is actively presented with the register assembly 6 together to its original position, wherein the three-dimensional physical world positions and available directions of objects 2 are known by previous measurement regarding to the register tracking tool 1. The world "actively" indicates that the tracking tool (1 or 4) is coupled to the tracking system and is getting its six-degree position and direction parameters.

The relative reference tracking tool 4 is fixedly attached on or inside the patient during the said registering time and later on during the surgical procedure. While keep the register assembly 6 remain on its original position as that during imaging scanning (in order other words, keep the relative position and direction between the register assembly 6 and the patient remain fixed), record the six-degree position and direction parameters of the register tracking tool 1 and of the relative reference tracking tool 4 regarding to the tracking system's frame, expressed by a 4×4 transform matrix B and a 4×4 transform matrix A respectively as shown in FIG. 1. The form of the 4×4 transform matrices A and B are as follows:

$$\begin{pmatrix} & & & x \\ & R & & y \\ & & & z \\ 0 & 0 & 0 & 1 \end{pmatrix}$$

R is the 3×3 rotation matrix. x, y, z are the coordinates of the tracking tool's position in the tracking system's frame.

Regarding to the frame of the register tracking tool 1, the six-degree position and direction parameters of the relative reference tracking tool 4 can be further expressed as:

$$C = B^{-1} * A \tag{12}$$

wherein $B^{-1}$ is the inverse matrix of matrix B for the register tracking tool 1 and C is a 4×4 matrix. Then a new TT can be defined and computed as:

$$TT = T*C = T*B^{-1}*A \tag{13}$$

wherein TT is a constant 4×4 matrix, regarded as a registered transform matrix, reflecting the specific relationship between patient world space and the scanned image space. The registered transform matrix TT is the transform for the relative reference tracking tool 4 to be transformed to the image space from its pose regarding to the tracking system's frame. During the registering time the specific relationship expressed by matrix TT are locked and computed.

There are several factors are locked during the registering time herein. The first one is that the relative reference tracking tool 4 is fixedly attached on or inside the patient (more specifically, the patient's region of interest for procedure). In other words, the relative position and the direction between the relative reference tracking tool 4 and the patient's region of interest for procedure are fixed during the registering time (and during the later surgical procedure). Although the placement of the relative reference tracking tool 4 is fixed relative to the patient, the relative reference tracking tool 4 is removable and can be turned back to its original position after removal. The locked second factor is that the register tracking tool 1 is fixedly placed on the register assembly 6 on its original position, wherein the three-dimensional physical world positions and available directions of objects 2 are previously measured regarding to the register tracking tool 1. The third locked factor is that the register assembly 6 is on its original position during imaging scanning, wherein the relative position and direction between the register assembly 6 and the patient are fixed. The fourth locked factor is that the pose relationships are rigid among the patient's region of interest for surgical procedure, the register tracking tool 1 and the relative reference tracking tool 4. In other words, there are no relative positions and directions change among the patient's region of interest for surgical procedure, the register tracking tool 1 and the relative reference tracking tool 4.

Figure 10:
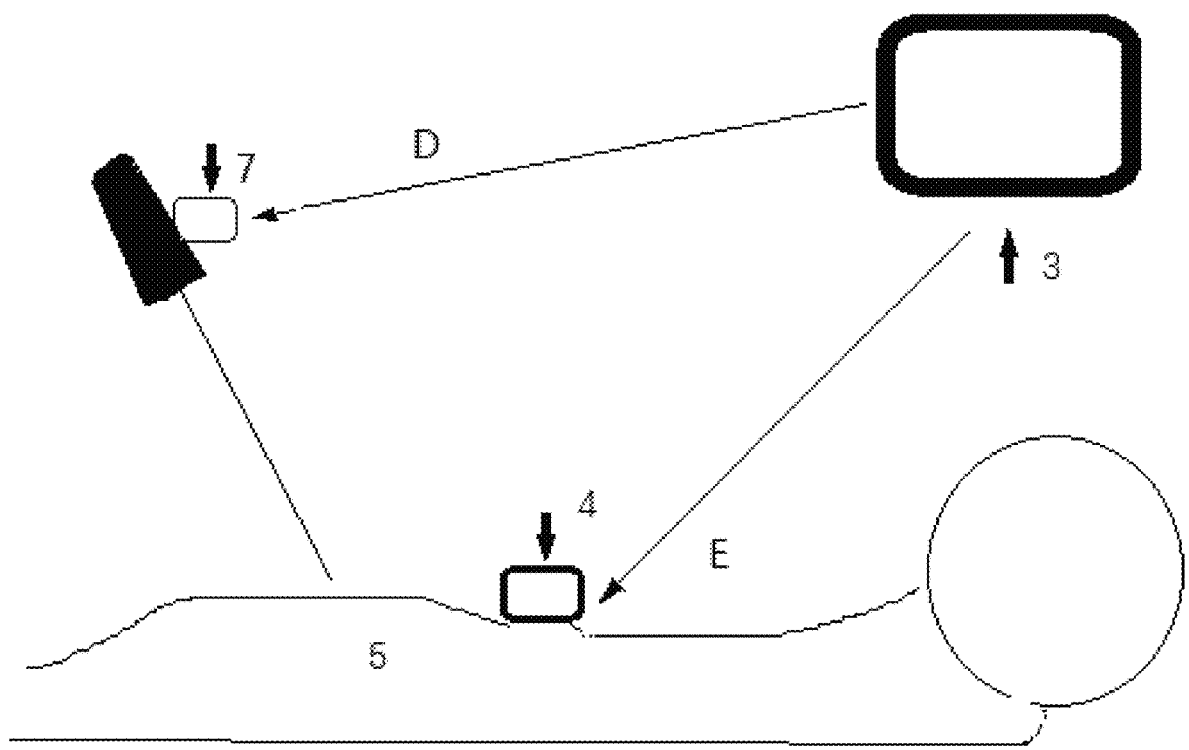
FIG. 10 a schematic diagram of tracking an instrument after registering.

After the registered transform matrix is decided, a surgical navigation system will start to work to assist a surgical procedure, while the register assembly 6 with the register tracking tool 1 are not necessarily present or can be removed from the patient. Surgical instruments (needles, ultrasound probes) are tracked with tracking tool 7 attached hereon as shown in FIG. 10. A surgical instrument's pose can use tracking tool 7's pose to represent. For example, after calibrating between the needle instrument's tip and the origin zero position of the tracking tool 7, the needle instrument's tip is known via the tracking tool 7. The tracking tool 7's pose is obtained via the tracking system and can be expressed by a 4×4 transform matrix D regarding to the tracking system's frame. Its pose regarding to the frame of the relative reference tracking tool 4 attached still on the surface on or inside the body of the patient can be expressed as $E^{-1}*D$, wherein the relative reference tracking tool 4's pose is expressed as a 4×4 matrix E regarding to the frame of the tracking system. The form of the 4×4 transform matrices D and E are as follows:

$$\begin{pmatrix} & & & x \\ & R & & y \\ & & & z \\ 0 & 0 & 0 & 1 \end{pmatrix}$$

R is the 3×3 rotation matrix. x, y, z are the coordinates of the tracking tool's position in the tracking system's frame.

It is noted that matrix E is not necessarily to be the same as matrix A, because the patient body may move from its original place. Since the registered transform matrix TT is decided already, the tracking tool 7's pose in image space converted from physical space can be furtherly expressed as follows:

$$F = TT*E^{-1}*D$$

$$\text{or } F = T*B^{-1}*A*E^{-1}*D \tag{14}$$

If the position of the tracking tool 7 regarding to the frame of the tracking system expressed by OBJECTW (x, y, z) is from the fourth column of D, the position in image space expressed by OBJECTM (x, y, z) can be obtained from the fourth column of F. If the tracking tool 7 has only three positional data rather than six-degree freedom data including rotation information, its corresponding image position can be computed via equation (14).

Similarly, if the tracking tool 7 has only directional data rather than positional data, its corresponding direction in image space can also be computed via equation (14) by considering the first 3 rows and the first 3 columns of matrices.

FIG. 11A and FIG. 11B show a flow chart of an embodiment to register positions and directions in image space with that in world space.

In some embodiments, the tracking tool with six-degree freedom of position and directions is composed with several tracking tools with less than six-degree freedom.

In some embodiments, the third orthogonal direction can be deduced from two orthogonal directions.

There are some other embodiments. For example, there are more than one register assembly and/or there are more than one register tracking tool removably attached on the register assembly(s). In some embodiments, there are more than one relative reference tracking tools on or in a patient body. In some embodiments, the relative tracking tool(s) on or in the body is(are) combined with the tracking tool(s) attached on the assembly. More components integrated are to have a better accuracy of registration and navigation.

There are distinguish advantages with the present disclosure of Measuring and Registering Method as descript below.

Since the register assembly 6 includes objects for registering with known positions and available directions, there is no need for a surgeon to deal with each object for registering. The registering tasks of existing methods, for example, could be to attach each object to the patient, to obtain its physical world position, and to map it to its corresponding image one by one. The present disclosure of registering method avoids such tasks.

Positions and available directions of objects on the assemble are measured in an easy way with a measuring piece. The measuring piece does not need calibration for its tip or direction with regard to the tracking tool attached on it. The measuring piece can directly measure positions and available directions of objects on the assemble without prior calibration according to the present disclosure.

It is convenient for imaging scanning. There is no need for tracking tools to be scanned. Just the assembly 6 and patient body are needed to be scanned. The tracking tool planned to be attached on the assembly is not needed during imaging scanning. The relative tracking tool planned to be put on the patient body is not needed during imaging scanning. This is an important advantage when taking MR imaging scanning. Some tracking tool has metal component. Metals are recommended not to use when taking MR imaging scanning.

The relative tracking tool 4 can be placed on the surface of the patient or inside the patient body freely and independently, without considering the placement of the assembly 6 and the attached tracking tool 1. After the registering time of recording pose parameters of the relative tracking tool 4 and the tracking tool 1 attached on the assembly 6, the patient is allowed to move to a different bed or to go to a different operation room, as long as the original position of the relative reference tracking tool 4 is still. In some embodiments, there is a small base/holder fixedly attached on the patient to allow the relative reference tracking tool 4 to be placed back to the base/holder on its original position. The patient just can move while keeping the small base/holder fixedly on the body. In some embodiments, a positional pen-mark is made on the patient for the relative reference tracking tool 4 to be placed back to its original position.

Since the reference frame is based on the patient (on the surface of the patient body or inside the patient body for some anatomic organs), when the patient/some organs move, the navigation of image display for relative positions and directions among the patient and surgical instruments will be still coincident correctly. In some embodiments, the relative reference tracking tool 4 or its holder can be inserted into an organ of the patient. If the organ moves because of respiration or other reason, the navigation of image display will not be affected and still be correct. The relative reference tracking tool 4 and its holder can be small enough for just attaching on the patient or inserting into the patient.

Registering is simple and quick. Just attach the relative reference tracking tool 4 to the patient and take records instantly of the six-degree pose parameters of the relative reference tracking tool 4 and the register tracking tool 1 via the tracking system. In some embodiments, it is just one button click for a surgeon to do. After recording pose parameters, the register assembly 6 can be detached from the patient.

The tracking system can employ one or more different types of positioning methods and devices, such as an electromagnetic tracking system, an optical tracking system, radio frequency (RF) tracking system, ultrasound tracking system, etc.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

Those of ordinary skill in the art will recognize that the functional blocks, methods, units, devices, and systems described in the present disclosure may be integrated or divided into different combinations of systems, units, devices, and functional blocks. Any suitable programming languages and programming techniques may be used to implement the routines of particular embodiments. Different programming techniques may be employed such as procedural or object-oriented. The routines may execute on a single processing device or multiple processors. Although the steps, operations, or computations may be presented in a specific order, the order may be changed in different particular embodiments. In some particular embodiments, multiple steps shown as sequential in this disclosure may be performed at the same time.

In some embodiments, a software or program code is provided to realize the method described above.

The invention claimed is:

1. A method of measuring and registering positions and directions in an image space with positions and directions in a world space, the method comprising:

a) providing an assembly and a tracking tool with six-degree freedom of positions and directions, wherein:

the assembly includes objects including: either at least four noncoplanar positional objects, or at least one positional object and at least three orthogonal directional objects;

the objects are rigidly placed in the assembly;

the tracking tool is removably attached on the assembly rigidly, such that three-dimensional positions and available directions of the objects and positions and directions of the tracking tool are fixed relatively each other in the world space;

the three-dimensional positions and the available directions of the objects in the world space are measured relative to a frame of the tracking tool; and the objects are configured to be scanned with imaging systems to obtain three-dimensional positions and available directions in the image space;

b) placing the assembly on a body rigidly and taking imaging scanning with an imaging system to thereby obtain the three-dimensional positions and the available directions of the objects in the image space;

c) computing a transformation of converting positions and directions from the world space into the image space, based on the three-dimensional positions and the available directions of the objects in the world space relative to the frame of the tracking tool measured in step a) and the three-dimensional positions and the available directions of the objects in the image space obtained in step b);
d) placing a relative tracking tool with six-degree freedom of positions and directions on or in a target;
with a tracking system, in a same time as a registering time, recording data of six-degree freedom of directions and positions for both the relative tracking tool and the tracking tool attached on the assembly with reference to the frame of the tracking system;
e) placing an instrument tracking tool on an instrument to track pose of the instrument;
with the tracking system, in a same time as a post-registering time, recording both data of positions and/or available directions of the instrument tracking tool attached on the instrument and data of six-degree freedom of positions and directions of the relative tracking tool with reference to the frame of the tracking system;
f) combining the transformation obtained in step c), the data recorded during the registering time in step d) and the data recorded during the post-registering time in step e), to compute the positions and/or the available directions of the instrument tracking tool attached on the instrument in the image space.

2. The method of claim 1, wherein the transformation is expressed as T, satisfying a relationship:

$$OBJECTM1_i^T = T * OBJECTW1_i^T \quad \text{equation (1)},$$

wherein
$OBJECTM1_i^T$ is a transpose matrix of $OBJECTM1_i$, OBJECTM1 represents (x,y,z,1) with (x,y,z) representing a position in the image space; $OBJECTW1_i^T$ is a transpose matrix of OBJECTW1, $OBJECTW1_i$ represents (x,y,z,1) with (x,y,z) representing a position in the world space in the frame of the tracking tool attached on the assembly removably and rigidly, i represents i th position of the objects with i>=4; a form of a 4×4 transform matrix T is as follows:

$$\begin{pmatrix} & & & x \\ & R & & y \\ & & & z \\ 0 & 0 & 0 & 1 \end{pmatrix},$$

wherein R is a 3×3 rotation matrix and x, y, z are translations of coordinates;
T is computed by solving simultaneous equations of at least four relationships of the equation (1) for at least 4 noncoplanar positions.

3. The method of claim 1, wherein the transformation is expressed as T, satisfying a relationship:

$$OBJECTM2_i = T * OBJECTW2_i \quad \text{equation (2)}$$

wherein
$OBJECTM2_i$ is a 4×4 matrix and is as follows:

$$\begin{bmatrix} Ax^M & Ay^M & Az^M & x \\ Bx^M & By^M & Bz^M & y \\ Cx^M & Cy^M & Cz^M & z \\ 0 & 0 & 0 & 1 \end{bmatrix},$$

wherein $(Ax^M, Ay^M, Az^M)$ are x, y, z cosine components of direction A in the image space; $(Bx^M\ By^M\ Bz^M)$ are x, y, z cosine components of direction B in the image space; $(Cx^M\ Cy^M\ Cz^M)$ are x, y, z cosine components of direction C in the image space; x, y, and z are position components in the image space;
$OBJECTW2_i$ is a 4×4 matrix and is as follows:

$$\begin{bmatrix} Ax^W & Ay^W & Az^W & x \\ Bx^W & By^W & Bz^W & y \\ Cx^W & Cy^W & Cz^W & z \\ 0 & 0 & 0 & 1 \end{bmatrix}$$

wherein $(Ax^W Ay^W Az^W)$ are x, y, z cosine components of direction A in the world space; $Bx^W By^W Bz^W)$ are x, y, z cosine components of direction B in the world space; $(Cx^W Cy^W Cz^W)$ are x, y, z cosine components of direction C in the world space; x, y and z are position components in the world space; wherein the positions and directions in the world space are in the frame of the tracking tool attached on the assembly removably and rigidly; i represents i-th position of the objects with i>=1;
a form of T is as follows:

$$\begin{pmatrix} & & & x \\ & R & & y \\ & & & z \\ 0 & 0 & 0 & 1 \end{pmatrix};$$

wherein R is a 3×3 rotation matrix and x, y, z are translations of coordinates;
T is obtained by solving at least one equation (2) for at least one position (x,y,z) and three orthogonal directions of A, B and C;
R is also obtainable by solving:

$$M * R = W \quad \text{equation (3)},$$

wherein M is a 3×3 matrix and is as follows:

$$\begin{pmatrix} Ax^M & Ay^M & Az^M \\ Bx^M & By^M & Bz^M \\ Cx^M & Cy^M & Cz^M \end{pmatrix},$$

W is a 3×3 matrix and is as follows:

$$\begin{pmatrix} Ax^W & Ay^W & Az^W \\ Bx^W & By^W & Bz^W \\ Cx^W & Cy^W & Cz^W \end{pmatrix}.$$

4. The method of claim 1, wherein, during the registering time, recorded positions and directions for both the tracking tool attached on the assembly and the relative tracking tool are expressed as a 4×4 matrix B and a 4×4 matrix A, respectively; during the post-registering time, recorded positions and available directions of the instrument tracking tool attached on the instrument are expressed as a 4×4 matrix D; during the post-registering time, recorded positions and directions of the relative tracking tool are expressed as a 4×4 matrix E; the positions and the available directions in the image space converted from the positions and the available directions in the world space for the instrument tracking tool attached on the instrument are expressed as a 4×4 matrix F, which satisfies a relationship:

$$F=T*B^{-1}*A*E^{-1}*D \qquad \text{equation (4)}$$

where T is the the transformation of converting positions and directions from the world space into the image space computed in step c); a form of T is as follows:

$$\begin{pmatrix} & & & x \\ & R & & y \\ & & & z \\ 000 & & & 1 \end{pmatrix},$$

wherein R is a 3×3 rotation matrix and x, y, z are translations of coordinates;
each matrix of B, A, E, D and F is as follows:

$$\begin{pmatrix} & & & x \\ & R & & y \\ & & & z \\ 000 & & & 1 \end{pmatrix},$$

wherein R is the 3×3 rotation matrix and x, y, z are positions of the components;
with three positional data of the instrument tracking tool in the world space with reference to the frame of the tracking system, corresponding image positions are computed via equation (4); with directional data of the instrument tracking tool in the world space with reference to the frame of the tracking system, corresponding directions in the image space are computed via equation (4).

5. The method of claim 1, wherein there are multiple assemblies and/or there are multiple tracking tools attached on the one or more of the multiple assemblies removably; and/or there are multiple relative tracking tools on or in the target, and/or one or more of the multiple relative tracking tools on or in the target is(are) combined with one or more of the multiple tracking tools attached on the assembly.

6. The method of claim 1, wherein the tracking tool with six-degree freedom of positions and directions attached on the assembly or the relative tracking tool with six-degree freedom of positions and directions placed on or in the target comprises a plurality of tracking tools with less than six-degree freedom.

7. The method of claim 1, wherein a third orthogonal direction is deduced from two orthogonal directions.

8. The method of claim 1, where the tracking system comprises at least one of electromagnetic tracking systems or optical tracking systems.

9. The method of claim 1, wherein positions of the positional objects are measured with reference to the frame of the tracking tool attached on the assembly with measuring steps comprising:

(i) providing one of the positional objects with a convex measuring surface, configured to be part or whole of a sphere, such that a center of the convex measuring surface substantially corresponds to a position of the one of the positional objects to be measured;

(ii) providing a measuring piece having a concave measuring surface substantially fitting with the convex measuring surface of the one of the positional objects;

(iii) attaching a measuring tracking tool with a six-degree freedom onto the measuring piece rigidly;

(iv) keeping the concave measuring surface touching seamlessly the convex measuring surface, such that a center of the concave measuring surface is unchanged, while moving the measuring piece at different positions; applying a measuring tracking system, recording data of directions and positions at at least two different positions of the measuring tracking tool attached on the measuring piece with reference to a frame of the measuring tracking system, concurrently recording data of directions and positions of the tracking tool attached on the assembly with reference to the frame of the measuring tracking system;

(v) with data recorded in step (iv), computing the center of the concave measuring surface of the measuring piece that is unchanged or the position of the one of the positional objects that is unchanged with reference to the frame of the tracking tool attached on the assembly.

10. The method of claim 9, wherein
the one of the positional objects comprises a first portion and a second portion;
the first portion has a shape of a sphere and a center of the spherical shape of the first portion is substantially at the center of the convex measuring surface;
the second portion is at an outer layer of the one of the positional objects and is arranged such that a center of the second portion also substantially coincides with the center of the convex measuring surface; and
the first portion and the second portion have different compositions capable of generating substantially different signals by a diagnostic imaging scanner, such that in the image space a position of the center of the spherical shape of the first portion is determined and measured accurately with a distinguishingly displayed spot.

11. The method of claim 9, wherein recorded data of the measuring tracking tool attached on the measuring piece are expressed as a 4×4 matrix $B_i$; recorded data of the tracking tool attached on the assembly are expressed as a 4×4 matrix $A_i$; positions and directions of the measuring tracking tool attached on the measuring piece in the frame of the tracking tool attached on the assembly are expressed as a 4×4 matrix $C_i$, satisfying a relationship:

$$C_i=A_i^{-1}*B_i \qquad \text{equation (5)},$$

wherein a form of the 4×4 transform matrices $A_i$, $B_i$ and $C_i$ is:

$$\begin{pmatrix} & & & x \\ & R & & y \\ & & & z \\ 000 & & & 1 \end{pmatrix};$$

wherein R is a 3×3 rotation matrix; x, y, z are component positions; i represents i th position with i>=2;
unchanged positions of the center of the concave measuring surface of the measuring piece in the frame of the tracking tool attached on the assembly are expressed by $X_S$, $Y_S$, $Z_S$, satisfying a relationship:

$X_S = X_{B_i} + X_o * C_i(1,1) + Y_o * C_i(2,1) + Z_o * C_i(3,1)$ $Y_S = Y_{B_i} + X_o * C_i(1,2) + Y_o * C_i(2,2) + Z_o * C_i(3,2)$ $Z_S = Z_{B_i} + X_o * C_i(1,3) + Y_o * C_i(2,3) + Z_o * C_i(3,3)$     equation (6);

wherein
- $X_O$, $Y_O$, $Z_O$ are offset distances from a center of the measuring tracking tool to the center of the concave measuring surface;
- $C_i$(m, n) are rotation elements of matrix $C_i$;
- $X_{B_i}$, $Y_{B_i}$, $Z_{B_i}$ are X, Y, Z positions of matrix $C^i$; and
- at least two group of equation (6) with i>=2 are solved to obtain measured position ($X_S$, $Y_S$, $Z_S$) of the center of the concave measuring surface or the center of the one of the positional objects in the frame of the tracking tool attached on the assembly.

12. The method of claim 9, wherein recorded data of the measuring tracking tool attached on the measuring piece with reference to the frame of the measuring tracking system are expressed as a 4×4 matrix $B_i$; recorded data of the tracking tool attached on the assembly with reference to the frame of the measuring tracking system are expressed as a 4×4 matrix $A_i$;

a form of the 4×4 transform matrices $A_i$ and $B_i$ is:

$$\begin{pmatrix} & & & x \\ & R & & y \\ & & & z \\ 0 & 0 & 0 & 1 \end{pmatrix};$$

wherein
- R is a 3×3 rotation matrix; x, y, z are component positions; i represents i th position with i>=2;
- unchanged positions of the center of the concave measuring surface of the measuring piece in the frame of the measuring tracking system are expressed by $X_S$, $Y_S$, $Z_S$, satisfying a relationship:

$X_S = X_{B_i} + X_O * B_i(1,1) + Y_O * B_i(2,1) + Z_O * B_i(3,1)$ $Y_S = Y_{B_i} + X_O * B_i(1,2) + Y_O * B_i(2,2) + Z_O * B_i(3,2)$ $Z_S = Z_{B_i} + X_O * B_i(1,3) + Y_O * B_i(2,3) + Z_O * B_i(3,3)$     equation (7);

wherein
- $X_O$, $Y_O$, $Z_O$ are offset distances from a center of the measuring tracking tool to the center of the concave measuring surface;
- $B_i$(m, n) are rotation elements of matrix $B_i$;
- $X_{B_i}$, $Y_{B_i}$, $Z_{B_i}$ are X,Y,Z positions of matrix $B_i$;
- at least two groups of equation (7) with i>=2 are solved to get measured positions ($X_S$, $Y_S$, $Z_S$) of the center of the concave measuring surface or of the object in the frame of the measuring tracking system;
- AA represents an inverse of mean of group of $A_i$ or one of $A_i$, and ($X'_S$, $Y'_S$, $Z'_S$) represent measured positions of the center of the concave measuring surface or of the one of the positional objects in the frame of the tracking tool attached on the assembly, ($X'_S$, $Y'_S$, $Z'_S$) are obtained based on:

$X'_S = X_B + X_S * AA(1,1) + Y_S * AA(2,1) + Z_S * AA(3,1)$ $Y'_S = Y_B + X_S * AA(1,2) + Y_S * AA(2,2) + Z_S * AA(3,2)$ $Z'_S = Z_B + X_S * AA(1,3) + Y_S * AA(2,3) + Z_S * AA(3,3)$     equation (8);

AA(m, n) are rotation elements of matrix AA; $X_B$, $Y_B$, $Z_B$ are X, Y, Z positions of matrix AA.

13. The method of claim 1, wherein directions of the directional objects are measured with reference to the frame of the tracking tool attached on the assembly, with measuring steps comprising:

(A) providing one of the directional objects with a measuring surface with a partial or full cylindrical convex groove or otherwise an elongated measuring surface, having at least a first partial or full circular cross section, and a second partial or full circular cross section, such that an axis of the cylindrical convex groove or the elongated measuring surface is coincident with a direction of the one of the directional objects;

(B) providing a measuring piece having a concave groove or partial or full-cylindrical cavity measuring surface, having at least two concave partial or full circular cross sections, substantially fitting with the convex measuring surface of the one of the directional objects;

(C) attaching a measuring tracking tool configured at least for directional tracking, onto the measuring piece rigidly;

(D) keeping the concave measuring surface touching seamlessly the convex measuring surface of the one of the directional objects, such that a direction of the axis of the concave measuring surface is unchanged, while rotating the measuring piece at different rotation angles; applying a measuring tracking system, in a same time, recording both data of directions at at least two different rotation angles of the measuring tracking tool attached on the measuring piece with reference to the frame of the measuring tracking system, and data of directions and positions of the tracking tool attached on the assembly with reference to the frame of the measuring tracking system;

(E) with the recorded data in step (D), computing the direction of the axis of the concave measuring surface of the measuring piece or of the one of the directional objects with reference to the frame of the tracking tool attached on the assembly.

14. The method of claim 13, wherein the one of the directional objects comprises a first portion and a second portion; and the first portion has an elongated shape and has an axis that coincides with the direction of the one of the directional objects; and the second portion is at an outer layer of the one of the directional objects and is arranged such that an axis of the second portion also substantially coincides with the axis of the first portion; and the first portion and the second portion have different compositions capable of generating substantially different signals by a diagnostic imaging scanner such that in the image space, an image direction of the axis of the first portion of the one of the directional objects is determined and measured accurately with a distinguishingly displayed line.

15. The method of claim 13, wherein recorded data of the measuring tracking tool attached on the measuring piece with reference to the frame of the measuring tracking system are expressed as a 4×4 matrix $B_i$; recorded data of the tracking tool attached on the assembly with reference to the frame of the measuring tracking system are expressed as a 4×4 matrix $A_i$;

wherein a form of the 4×4 matrices $A_i$, and $B_i$ is:

$$\begin{pmatrix} & & & x \\ & R & & y \\ & & & z \\ 0 & 0 & 0 & 1 \end{pmatrix},$$

wherein R is a 3×3 rotation matrix; x, y, z are component positions; i represents i th position with i>=2;
the direction of the axis of the concave measuring surface of the measuring piece in the frame of the measuring tracking system is expressed by δx δy, δz, satisfying a relationship:

$$\delta x = X_{off} * B_i(1,1) + Y_{off} * B_i(2,1) + Z_{off} * B_i(3,1)$$

$$\delta y = X_{off} * B_i(1,2) + Y_{off} * B_i(2,2) + Z_{off} * B_i(3,2)$$

$$\delta z = X_{off} * B_i(1,3) + Y_{off} * B_i(2,3) + Z_{off} * B_i(3,3) \qquad \text{equation (9)};$$

wherein $X_{off}$, $Y_{off}$, $Z_{off}$ are component directional offsets /calibration parameters between directions of the measuring tracking tool attached on the measuring piece and the direction of the axis of the concave measuring surface of the measuring piece; $B_i(m, n)$ are rotation elements of matrix $B_i$; at least two group of equation (9) with i>=2 are solved to get (δx, δy, δz);
AA represents an inverse of mean of group of $A_i$ or one of $A_i$, and (δ'x, δ'y, δ'z) represent a measured direction of the axis of the concave measuring surface of the measuring piece or of the one of the directional objects in the frame of the tracking tool attached on the assembly, and the (δ'x, δ'y, δ'z) are calculated from:

$$\delta' x = \delta x * AA(1,1) + \delta y * AA(2,1) + \delta z * AA(3,1)$$

$$\delta' y = \delta x * AA(1,2) + \delta y * AA(2,2) + \delta z * AA(3,2)$$

$$\delta' z = \delta x * AA(1,3) + \delta y * AA(2,3) + \delta z * AA(3,3) \qquad \text{equation (10)},$$

wherein AA(m, n) are rotation elements of matrix AA.

16. The method of claim 13, wherein recorded data of the measuring tracking tool attached on the measuring piece are expressed as a 4×4 matrix $B_i$; recorded data of the tracking tool attached on the assembly are expressed as a 4×4 matrix $A_i$; the pose of the measuring tracking tool attached on the measuring piece in the frame of the tracking tool attached on the assembly is expressed as a 4×4 matrix $C_i$, satisfying a relationship:

$$C_i = A_i^{-1} * B_i \qquad \text{equation (11)},$$

wherein a form of the 4×4 matrices $A_i$, $B_i$ and $C_i$ are as follows:

$$\begin{pmatrix} & & & x \\ & R & & y \\ & & & z \\ 0 & 0 & 0 & 1 \end{pmatrix};$$

wherein R is a 3×3 rotation matrix; x, y, z are component positions; i represents i th position with i>=2;
the direction of the axis of the concave measuring surface of the measuring piece or of the one of the directional objects in the frame of the tracking tool attached on the assembly is expressed by (δ'x, δ'y, δ'z), satisfying a relationship:

$$\delta' x = X_{off} * C_i(1,1) + Y_{off} * C_i(2,1) + Z_{off} * C_i(3,1)$$

$$\delta' y = X_{off} * C_i(1,2) + Y_{off} * C_i(2,2) + Z_{off} * C_i(3,2)$$

$$\delta' z = X_{off} * C_i(1,3) + Y_{off} * C_i(2,3) + Z_{off} * C_i(3,3) \qquad \text{equation (12)}$$

wherein $X_{off}$, $Y_{off}$, $Z_{off}$ are component directional offsets/calibration parameters between directions of the measuring tracking tool attached on the measuring piece and the direction of the axis of the concave measuring surface of the measuring piece; $C_i(m, n)$ are rotation elements of matrix $C_i$; and at least two groups of equation (12) with i>=2 are solved to get the measured direction of the axis of the concave measuring surface of the measuring piece or of the one of the directional objects in the frame of the tracking tool attached on the assembly.

* * * * *